(12) United States Patent
Dixit et al.

(10) Patent No.: US 8,669,348 B2
(45) Date of Patent: Mar. 11, 2014

(54) ANTI DIABETIC PROTEIN

(75) Inventors: Aparna Dixit, New Delhi (IN); Aruna Vashishta, New Delhi (IN); Tejram Sahu, New Delhi (IN); Shailesh Kumar Choudhary, New Delhi (IN); Alli Murugesan, New Delhi (IN)

(73) Assignee: Aparna Dixit, New Delhi (IN)

( * ) Notice: Subject to any disclaimer, the term of this patent is extended or adjusted under 35 U.S.C. 154(b) by 704 days.

(21) Appl. No.: 12/594,007

(22) PCT Filed: Mar. 28, 2008

(86) PCT No.: PCT/IN2008/000201
§ 371 (c)(1),
(2), (4) Date: Aug. 6, 2010

(87) PCT Pub. No.: WO2008/120240
PCT Pub. Date: Oct. 9, 2008

(65) Prior Publication Data
US 2011/0046054 A1    Feb. 24, 2011

(30) Foreign Application Priority Data

Mar. 30, 2007 (IN) .............................. 716/DEL/2007

(51) Int. Cl.
| | | |
|---|---|---|
| *A61K 38/00* | (2006.01) | |
| *A61K 38/10* | (2006.01) | |
| *A61K 38/16* | (2006.01) | |
| *A61K 38/04* | (2006.01) | |
| *A61P 3/10* | (2006.01) | |
| *C07K 4/10* | (2006.01) | |
| *C07K 1/14* | (2006.01) | |
| *C07K 7/08* | (2006.01) | |
| *C07K 14/415* | (2006.01) | |

(52) U.S. Cl.
USPC ........... 530/370; 530/324; 530/326; 530/344; 530/412; 514/6.8

(58) Field of Classification Search
USPC ............ 530/324, 326, 344, 370, 412; 514/6.8
See application file for complete search history.

(56) References Cited

U.S. PATENT DOCUMENTS 6,831,162 B2 * 12/2004 Khanna .......................... 530/350

FOREIGN PATENT DOCUMENTS

WO    00/61619    10/2000

OTHER PUBLICATIONS

Vashishta et al., 2006, In vitro refolded napin-like protein of *Momordica charantia* expressed in *Escherichia coli* displays properties of native napin, Biochimica et Biophysica Acta, 1764: 847-855.*
Neumann et al., 1996, Purification and sequencing of napin-like protein small and large chains from *Momordica charantia* and *Ricinus communis* seeds and determination of sites phosphorylated by plant Ca2+-dependent protein kinase, Biochimica et Biophysica Acta, 1298: 223-240.*
Terras, Franky R. G., et al. "A new family of basic cysteine-rich plant antifungal proteins from *Brassicaceae* species" FEBS Letters, vol. 316, No. 3, 233-240 (Feb. 1993).

* cited by examiner

*Primary Examiner* — Amber D Steele
(74) *Attorney, Agent, or Firm* — Ladas & Parry LLP

(57) ABSTRACT

The present invention relates to a novel hypoglycemic/anti-hyperglycemic protein named ADMc1 purified from the seeds of *Momordica charantia* for control of hyperglycemia. The process for the purification of novel hypoglycemic/anti-hyperglycemic protein named ADMc1 is also disclosed. The invention also relates to process for preparation and purification of the recombinant novel hypoglycemic/anti-hyperglycemic protein of *Momordica charantia*, named rADMc1. Both ADMc1 and rADMc1 are highly effective and need to be administered only once a day to maintain normal blood glucose levels. The procedure involves purification of a novel hypoglycemic/anti-hyperglycemic protein of *M. charantia*, construction of cDNA library from *M. charantia* seeds, screening of cDNA library using oligonucleotide probe designed on the basis of amino acid sequence of the tryptic fragment of the protein, cloning of the cDNA in a eukaryotic expression system, expression and purification of the recombinant protein.

23 Claims, 8 Drawing Sheets

Figures 1, 2:
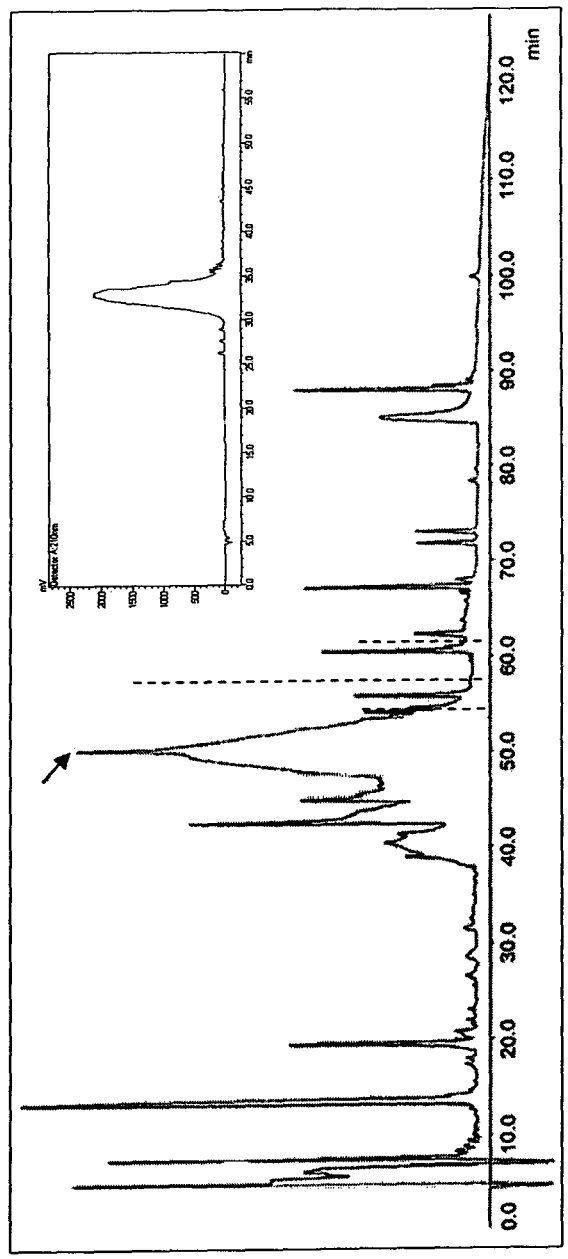

EVQSQQHGQQGSQILQHAR.

The sequence revealed this fraction to contain a novel protein as it did not match with any protein in the protein data base.

ANTI DIABETIC PROTEIN

CROSS-REFERENCE TO RELATED APPLICATIONS

This application is a 371 application of International Application PCT/IN08/00201, filed Mar. 28, 2008, which claims priority from Indian Patent Application 716/DEL/2007, filed Mar. 30, 2007.

FIELD OF INVENTION

The present invention relates to identification and purification of a novel anti-diabetic protein of *Momordica charantia*, its cDNA cloning and process for the production of the recombinant protein conferring anti-diabetic activity. In particular, the present invention relates to identification, isolation and characterization of anti-diabetic protein from *Momordica charantia*. The present invention also relates to a method for the manufacture of said protein by recombinant techniques.

BACKGROUND OF THE INVENTION

Diabetes mellitus is a metabolic disorder of multiple etiologies, characterized by chronic hyperglycemia with disturbances in carbohydrate, fat and protein metabolism resulting from defects in insulin secretion, insulin action, or both. The effects of diabetes mellitus include long-term damage, dysfunction and failure of various organs. Diabetes manifests with characteristic symptoms such as polyuria, polydipsia, weight loss, blurred vision, skin and genital infection [Taft, P., 1984, Pathogenesis, classification presentation, diagnosis and natural/history in diabetes mellitus, A guide to treatment, AIDS Health Science Press. pp: 1-10].

Earlier considered a disease of minor significance to world health, diabetes is taking its place as one of the main threats to human health in the 21$^{st}$ century after cancer and AIDS with an alarming rise in the number of diabetic cases every day. The past two decades have seen an explosive increase in the number of people diagnosed with diabetes worldwide. The global figure of people with diabetes is set to rise from the current estimate of 150 million to 220 million in 2010, and 300 million in 2025 [Amos et al., 1997, Diabetic Med. 14: S1-S85; King et al., 1998, Diabetes Care, 21: 1414-1431]. Recent report released by International Diabetes Federation (IDF) shows that 200 individuals develop diabetes every day [Diabetes voice, a publication of IDF, Nov. 15, 2006]. The Asia Pacific region is at the forefront of the current epidemic of diabetes which constitute 25% of the total 440,000 Type 1 diabetes worldwide under the age of 14 [Cockram, C. S., 2000, Hong Kong Med. J., 6: 43-52]. The Indian scenario is equally alarming, with the age and gender standardized prevalence rate of 4.3% [Sadikot S M, et al; Diabetes India., 2004, Diabetes Res Clin Pract. 66, 301-307]. This when translated into numbers clearly shows that the WHO estimate of the Indian diabetes burden of 35 million people by 2025 [King, H. et al., 1998, Diabetes Care, 21: 1414-1431] has been reached more than two decades earlier. This increase in incidence of diabetes in developing countries is due to the rapid increase in population, increased longevity and high ethnic susceptibility to diabetes coupled with rapid urbanization and lifestyle changes.

Chronic hyperglycemia during diabetes causes glycation of several proteins, thus leading to microvascular complications such as retinopathy, nephropathy, diabetic neuropathy etc. These may be delayed, lessened, or prevented by maintaining blood glucose levels close to normal. Hence, control of blood glucose on a 24 hour basis is the desired goal in the management of diabetes mellitus. Dieting, physical exercise [Bjorntorp, P., 1997, Nutrition 13:795403], insulin replacement therapy, and use of oral hypoglycemic/anti-hyperglycemic agents [Dunn, C. I and Peters; D. H., 1995; Drugs, 49: 721-49] have been employed for the treatment of this disorder, but not with desired success. Although euglycemia can be achieved in diabetic patients by conventional insulin therapy, complications such as hypoglycemia and lipoatropy can not be prevented. Moreover, the cost of insulin treatment is exorbitant, as it is required for the entire lifetime.

Besides the use of insulin, other therapeutic approaches for the control of hyperglycemia include the use of amylin analogues which regulate gastric emptying; inhibitors of intestinal alpha glucosidases like acarbose, miglitol and voglibiose which delay post prandial hyperglycemia; sulphonylureas, the most widely used class of drugs, that act by closure of ATP-dependent IC channel; Metformin, a biguanide that limits intestinal glucose absorption etc. However, these drugs have many adverse effects such as causing severe hypoglycemia at higher doses, liver problems, lactic acidosis and diarrhea [Reuser, A. J. and Wisselaar, H. A., 1994, Eur. J. Clin. Invest., 24(3): 19-24; Dunn and Peters, 1995, Drugs, 49: 721-49; Hillson, R., 1996, Oral hypoglycemic/anti-hyperglycemic treatment, in Practical Diabetes Care, Oxford University Press, pp 62-71].

Since the currently available treatment is expensive and far from satisfactory, alternate therapeutic approaches like the use of medicinal plants for controlling diabetes are gaining popularity among the scientific community.

Scientific investigations have established that *M. charantia* (bitter gourd) is highly beneficial in the treatment of diabetes in gerbils, langurs, and humans [Baldwa, V. S., et al, 1977, Upsala J. Med. Sci., 82: 39-41; Khanna, P. et al, 1981, J. Nat. Prod., 44: 648-55; Leatherdale, B. A et al, 1981, Br. Med. J. (Clin. Res. Ed.), 282: 1823-1824; Srivastava, Y., et al., 1988, Pharmacol. R. Commun., 20: 201-209]. These investigations strongly suggest the presence of compound(s) with insulinomimetic activities in *M. charantia* fruits and seeds [Welihinda et al., J. Ethnopharmacol., 17: 277-282, 1986; Srivastava et al., 1993, Phytother. Res. 7: 285-289]. Few attempts have been made to identify the active principles [Khanna, P. et al, (1981) J. Nat. Prod., 44: 648-55; Ng et al., 1986, J. Ethnopharmacol., 15: 107-117].

The published work of Khanna et al., [1981, J. Nat. Prod., 44: 648-55] and their Indian patents (No. 136565 and 176040) describe methods for the extraction of a protein called polypeptide-p from *M. charantia* fruits and tissue culture. The polypeptide-p is made of 166 amino acid residues and said to be of 11 kDa. The patent describes only the amino acid composition of the polypeptide-p but not the amino acid sequence of the protein. U.S. Pat. No. 6,831,162 describes purification of a hypoglycemic/anti-hyperglycemic protein, polypeptide-k isolated form the dry seeds of *M. charantia* possessing hypoglycemic/anti-hyperglycemic activity. The polypeptide-k is made up of 160 amino acid residues and is of 18 kDa. Like the Indian patents 136565 and 176040, this patent also gives only amino acid composition and does not disclose the amino acid sequence. Therefore, these molecules are not fully characterized.

Though several attempts have been made by many investigators to obtain a potential hypoglycemic/anti-hyperglycemic drug from *M. charantia*, it remains an illusion because of several reasons. Lack of systemic investigation, poor statistical analysis, wide variation in preparation technique and optimum dosage of bitter melon [Basch et al., 2003, Am. J. Health Syst. Pharm 60: 356-3591 are responsible for the failures of getting an universal principle from this highly potential medicinal plant. Apart from the above reasons, subtle differences in soil type and its subsequent effect on plant composition result in the variation in the isolated product. Impact of the variation in environmental condition, soil and plant subspecies also play a major role in its protein expression profile [Vallejos, 1991. Plant, Cell and Environment, 14: Page 105; ISB News Report, December, 2004), which influence the potential and reproducibility of the reported data. Production of proteins through recombinant DNA technology allows one to overcome these disadvantages and maintain the quality of the product.

Existing State of Art in Relation to Hypoglycemic/Anti-Hyperglycemic Proteins from *M. charantia*.

Indian patent 136565 describes a method for the extraction of a protein called polypeptide-p from *M. charantia* by using ethanol, diethyl ether and sulfuric acid.

Indian patent 176040 discloses another process claiming it to be more effective than the process described in Indian patent 136565 for the purification of polypeptide-p and uses hexane along with diethyl ether for purification.

U.S. Pat. No. 6,831,162 describes the invention of a novel hypoglycemic/anti-hyperglycemic protein of ~18 kDa designated as polypeptide-k and its method of extraction.

These patents though describe the procedure for extraction of hypoglycemic/anti-hyperglycemic proteins from *M. charantia*; they have several drawbacks:

1. Since the protein is isolated from the plant source, the quality of the isolated product depends on the quality of the raw material used. Since the constituents of the plants are greatly affected by the soil and environment, it is not always possible to get consistent quality of the final product.
2. Seasonal nature of the tropical plant makes it difficult to purify the peptide through out the year. The purification depends upon the availability of the raw material.
3. Extraction of proteins from plant source is time-consuming and cumbersome.
4. Extraction of these polypeptides involves the use of inflammable solvents such as diethyl ether, hexane etc. Use of highly inflammable organic solvents in extraction procedure is not desirable as it exposes the personnel to professional hazards.
5. These solvents are expensive and therefore the extraction is not economical.
6. The recovery of the purified protein is also very poor.
7. The presence of other contaminants in the raw material such as pesticides, insecticides and others affect the quality of the final product.
8. For both the polypeptide-p and polypeptide-k only the number of amino acids present in the protein, amino acid composition and their molecular mass are given. Thus, these proteins are not fully characterized and their primary structure (amino acid sequences) are not defined.

The present invention discloses a novel hypoglycemic/anti-hyperglycemic protein obtained from the seeds of *M. charantia*. The present invention further discloses the process for purification of the novel hypoglycemic/anti-hyperglycemic protein of *M. charantia* and the cloning of the gene encoding the novel hypoglycemic/anti-hyperglycemic protein of *M. charantia* and expression of this protein in eukaryotic expression system using recombinant DNA technology.

OBJECTS OF THE INVENTION

It is an important object of the present invention to identify, purify and characterize novel hypoglycemic/anti-hyperglycemic protein from the seeds isolated from the unripe fruits of *M. charantia* (named ADMc1).

Another object of the present invention is to determine the amino acid sequence of the novel hypoglycemic/anti-hyperglycemic protein of the *M. charantia*.

Still another object of the present invention is to screen the cDNA library made from the seeds isolated from the unripe fruits of *M. charantia*.

Another object of the present invention is to identify a full length cDNA encoding the novel hypoglycemic/anti-hyperglycemic protein of *M. charantia*.

Yet another object of the present invention is to clone and express the region of the cDNA encoding the novel hypoglycemic/anti-hyperglycemic protein of the *M. charantia* in eukaryotic expression system using *Pichia pastoris* as a host.

Still another object of the present invention is to produce recombinant hypoglycemic/anti-hyperglycemic protein for use as an anti-diabetic therapeutic agent.

SUMMARY OF THE INVENTION

The present invention discloses a novel hypoglycemic/anti-hyperglycemic protein named ADMc1 purified from the seeds of *Momordica charantia* having SEQ ID NO. 2.

In another embodiment the present invention discloses a cDNA, having SEQ ID NO. 5, encoding the novel hypoglycemic/anti-hyperglycemic protein named ADMc1 of *Momordica charantia*.

In still another embodiment the novel hypoglycemic/anti-hyperglycemic protein of the present invention is water soluble and is a member of 2S albumin family of proteins.

In yet another embodiment of the present invention the novel hypoglycemic/anti-hyperglycemic protein is of 12 kDa consisting of two chains of 8 kDa having SEQ ID NO: 3 and ~4 kDa having SEQ ID NO:4.

In another embodiment of the present invention the process for the purification of novel hypoglycemic/anti-hyperglycemic protein named ADMc1 from the seeds of *Momordica charantia* comprises the steps of (a) decorticating and powdering the seeds; (b) extracting seed proteins from the decorticated and powdered seeds obtained from step (a); (c) centrifugation of the seed proteins; (d) separation of soluble protein fraction and pelleted proteins wherein the soluble protein fraction is enriched in hypoglycemic/anti-hyperglycemic activity; and (e) purifying the hypoglycemic/anti-hyperglycemic proteins to homogeneity.

In still another embodiment of the present invention the decorticating and powdering is performed in liquid nitrogen.

In yet another embodiment of the present invention the extracting of seed proteins is performed with a mixture of buffered sulfuric acid ethanol or other acceptable extraction medium containing protease inhibitor phenylmethylsulfonyl fluoride (0.5-3 mM).

In another embodiment of the present invention the purification of novel hypoglycemic/anti-hyperglycemic protein is performed at 16,000-20,000×g for 1-2 h at 4° C. or by ultra-filtration or by salt and/or pH gradient.

In still another embodiment of the present invention the purification of the hypoglycemic/anti-hyperglycemic proteins is performed by subjecting the hypoglycemic/anti-hyperglycemic protein fraction to reverse-phase HPLC.

In yet another embodiment the present invention discloses the process for preparation and purification of the recombinant novel hypoglycemic/anti-hyperglycemic protein of *Momordica charantia*, named rADMc1, comprising the steps of (a) isolating and purifying mRNA from unripe fruits bearing developing seeds of *M. charantia*; (b) preparing cDNA from the purified mRNA; (c) isolating the cDNA encoding the novel hypoglycemic/anti-hyperglycemic protein; (d) cloning the isolated cDNA encoding the novel hypoglycemic/anti-hyperglycemic protein into an expression vector; (e) isolating DNA comprising the cloned cDNA encoding the novel hypoglycemic/anti-hyperglycemic protein; (f) transforming the DNA into Pichia pastoris; (g) cultivating Pichia pastoris containing the novel hypoglycemic/anti-hyperglycemic protein gene clone wherein the novel hypoglycemic/anti-hyperglycemic protein gene clone is cultivated by culturing said Pichia pastoris in culture medium to produce recombinant novel hypoglycemic/anti-hyperglycemic protein named rADMc1; and (h) purifying the recombinant novel hypoglycemic/anti-hyperglycemic protein from the culture medium.

In another embodiment of the present invention the Pichia pastoris is Pichia pastoris GS115.

In yet another embodiment of the present invention the expression vector is pPIC9K.

In still another embodiment of the present invention the culture medium is a combination of growth culture medium and induction culture medium.

In another embodiment of the present invention the growth culture medium is buffered minimal glycerol (BMG) medium and the induction culture medium is buffered minimal methanol (BMM) medium.

In yet another embodiment of the present invention the purification of recombinant novel hypoglycemic/anti-hyperglycemic protein is performed by one-step size exclusion chromatrography and about 70 mg of purified protein is obtained from 1 liter of induction culture.

In still another embodiment the present invention discloses a composition comprising novel hypoglycemic/anti-hyperglycemic protein of SEQ ID NO. 2 and excepients, a fragment thereof, a polypeptide bearing SEQ ID NO. 2, or an isoform of a polypeptide comprising of said SEQ ID NO. 2 or a modified polypeptide fragments consisting of portions of the said SEQ ID NO. 2 and portions thereof including fragments together with pharmaceutically acceptable carriers or in fusion with another protein/peptide, additives or adjuvants for the treatment of hyperglycemia wherein the novel hypoglycemic/anti-hyperglycemic protein is ADMc1 or recombinant novel hypoglycemic/anti-hyperglycemic protein of Momordica charantia, (rADMc1).

In another embodiment of the present invention the composition is a pharmaceutical composition. Various compositions consisting of carriers, vehicles, modulators, comprising of the polypeptide bearing SEQ ID NO. 2 and excepients, a fragment thereof, a polypeptide bearing SEQ ID NO:2, as an isoform of a polypeptide comprising of said SEQ ID NO: 2, or modified polypeptide fragments consisting of portions of the said SEQ ID NO: 2 and portions thereof including fragments together with pharmaceutically acceptable carriers or in fusion with another protein/peptide may be used for the treatment of hyperglycemia.

In yet another embodiment the present invention discloses the method of treating a mammal suffering from hyperglycemia which comprises administering to said mammal novel hypoglycemic/anti-hyperglycemic protein having SEQ ID NO. 2 or a pharmaceutical composition described above comprising said novel hypoglycemic/anti-hyperglycemic protein having SEQ ID NO. 2 wherein the novel hypoglycemic/anti-hyperglycemic protein is ADMc1 or rADMc1 of Momordica charantia.

In still another embodiment the present invention discloses the method of treating a mammal suffering from hyperglycemia wherein the mammal is an animal or human and the step of administration comprises oral administration, needle less administration, injection, sub-cutaneous, trans-dermal, intra-muscular, intra-peritoneal, pump delivery, inhalation, sub-lingual or combinations thereof.

In another embodiment of the present invention the novel hypoglycemic/anti-hyperglycemic protein does not cross react with insulin antibodies.

In yet another embodiment of the present invention a single dose administration of the novel hypoglycemic/anti-hyperglycemic protein brings down the blood glucose levels of hyperglycemic animals by 50-80%, (wherein subjects having hyperglycemic level are defined as with serum glucose concentration at greater than 300 mg/dL) and maintains the reduced blood glucose level of experimental diabetic subjects for upto 24 hr or more, and a single dose administration of 5-30 mg/kg body wt. per day does not show any side effect on the experimental subjects.

In still another embodiment the present invention discloses the use of novel hypoglycemic/anti-hyperglycemic protein of Momordica charantia having SEQ ID NO. 2 in the preparation of a medicament for the treatment of hyperglycemia wherein the novel hypoglycemic/anti-hyperglycemic protein is. ADMc1 or rADMc1 of Momordica charantia.

BRIEF DESCRIPTION OF ACCOMPANYING DRAWINGS

FIG. 1: Amino acid sequence of a tryptic fragment of 2160.32 Da (SEQ ID NO. 1) present in hypoglycemic/anti-hyperglycemic fraction obtained from M. charantia.

FIG. 2: Hypoglycemic/anti-hyperglycemic fraction of M. charantia is subjected to reverse phase high pressure liquid chromatography (RP-HPLC) to fractionate the proteins and to remove any degradation products by resolving on Discovery Wide pore C8 analytical column (5 µm particle size, 300 Å pore, 46×250 mm) using a gradient of 5-90% acetonitrile in aqueous 0.1% TFA. Flow rate is maintained at 0.5 mL/min for a run time of 120 min. The predominant peak (arrow) represents the hypoglycemic/anti-hyperglycemic protein peak of M. charantia. Inset shows the RP-HPLC profile of the purified peak protein.

Figure 3:
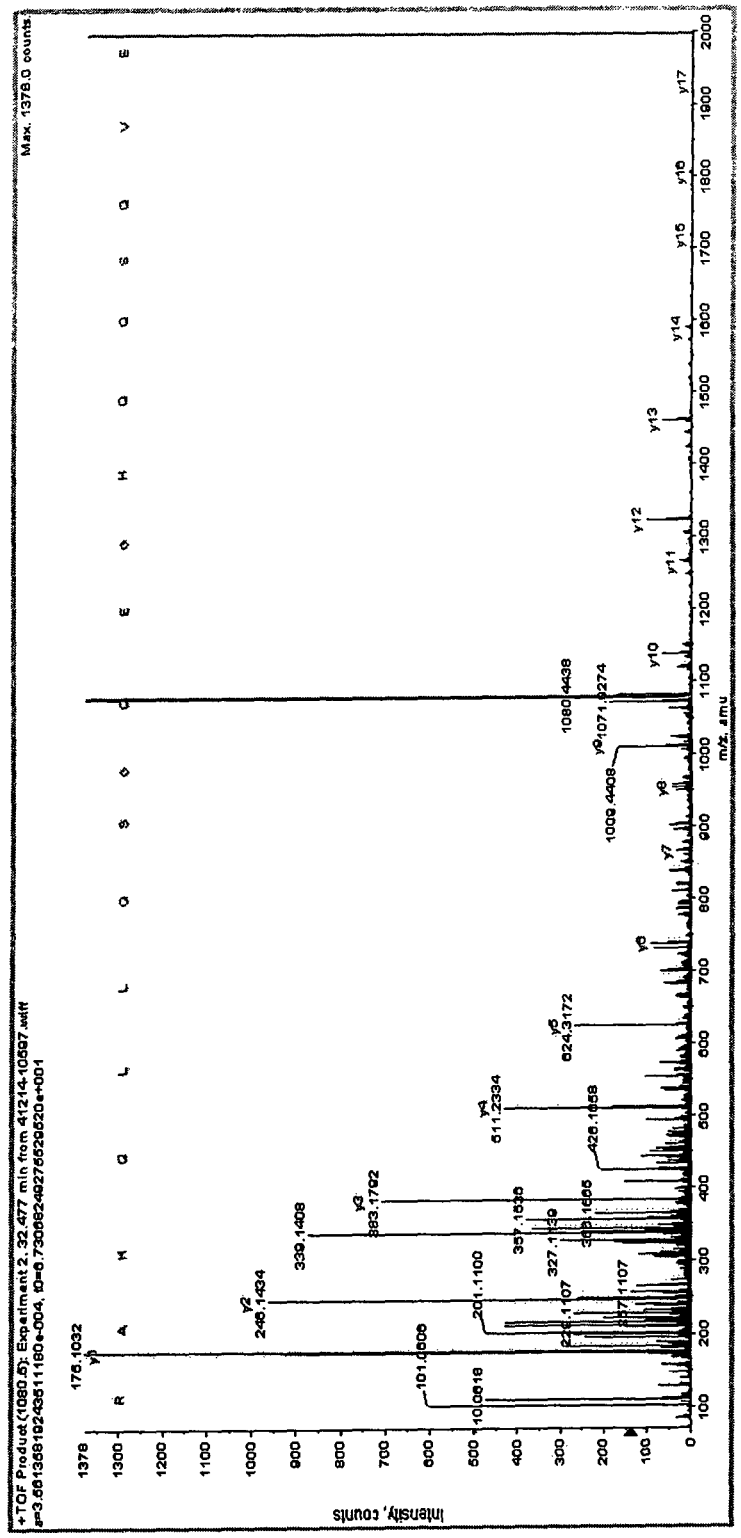

FIG. 3: Amino acid sequence of a tryptic fragment of ADMc1: Predicted amino acid sequence of a peptide of RP-HPLC purified hypoglycemic/anti-hyperglycemic protein [ADMc1] generated by tryptic digestion during MALDI-TOF Analysis (product ion 2159.02 Da) was analysed to obtain de novo protein sequence using Analyst QS software (Applied Biosystems)+TOF Product (1080.5), Precursor MW: 2159.02 MS/MS interpreted sequence.

Figure 4:
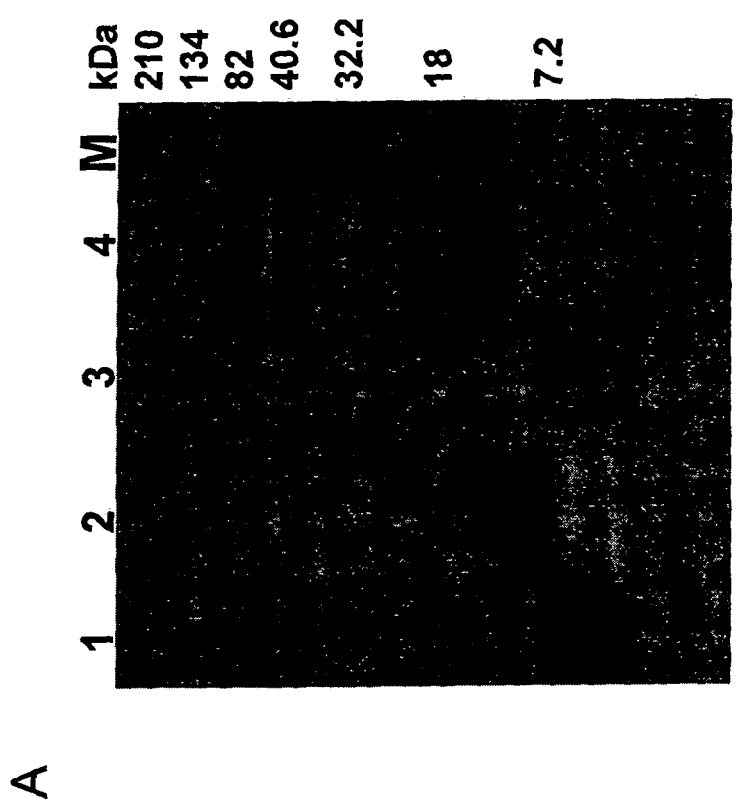

FIG. 4: (A) Analysis of the purified hypoglycemic/anti-hyperglycemic protein of M. charantia on 16.5% peptide gel using Tris-tricine buffer system: Lane M: protein molecular weight marker. Lanes 1 and 2 represent reduced and unreduced native hypoglycemic/anti-hyperglycemic protein samples. Lanes 3 and 4 represent reduced and unreduced deglycosylated (treated with deglycosylation enzyme, N-glycosidase (PNGase F, New England Biolabs, USA) protein samples.

The approximate mol. mass of the protein in unreduced form is calculated to be ~12 kDa. The protein is named as ADMc1. The purified ADMc1 gives a diffused appearance in native conditions on SDS-PAGE, which is a characteristic feature of glycosylated proteins. Deglycosylation of the protein with PNGase F resulted in sharpening of the bands lanes (3 and 4). (B) Confirmation of glycosylation status with Periodic acid/Schiff staining: Lane M: Parallely electrophoresed protein molecular weight markers stained by silver staining. Lane 1: Horse radish peroxidase (positive control). Lane 2: ADMc1.

Figure 5:
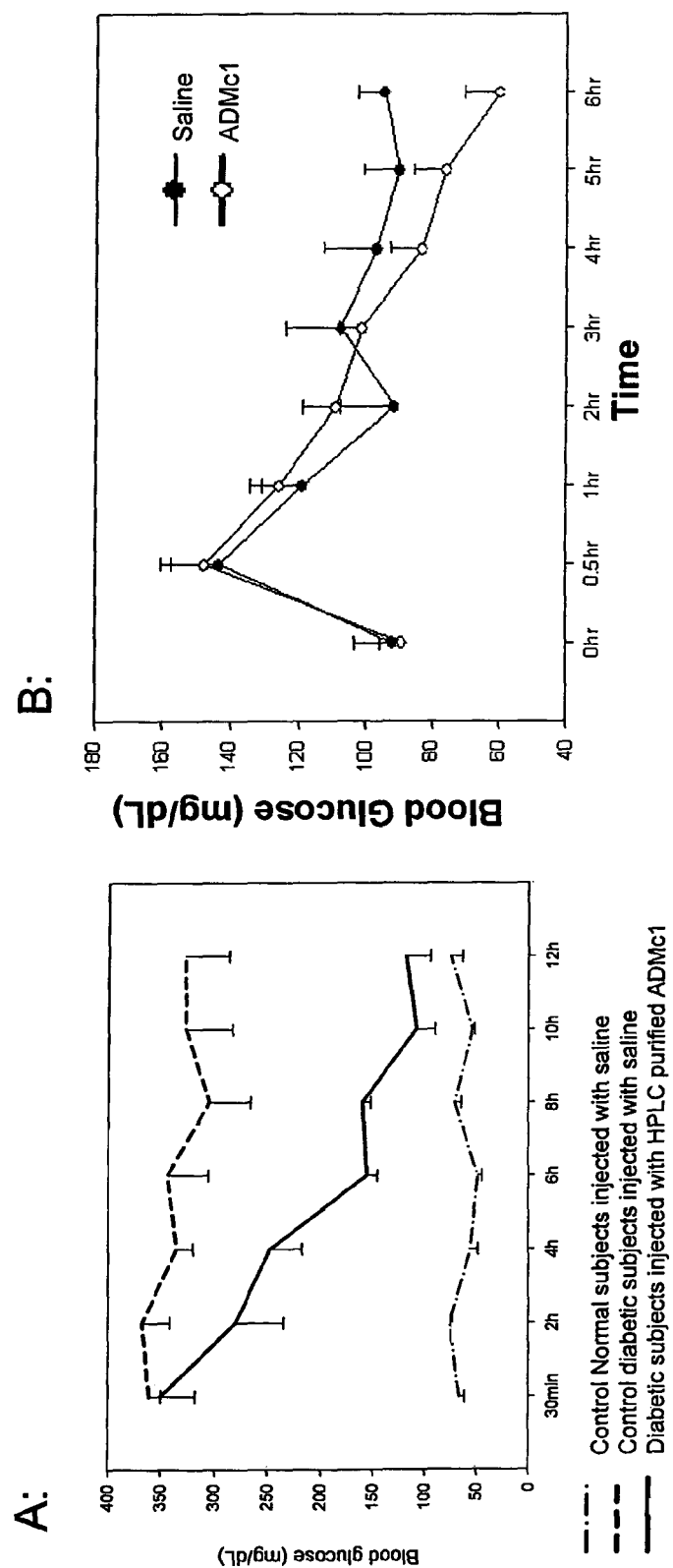

FIG. 5: (A) Blood glucose lowering ability of purified ADMc1 in diabetic animals: Diabetic animals were treated with ADMc1 (15 mg/kg body wt. each) or saline (equivalent volume of ADMc1) and blood glucose was estimated at different time points. The data represent mean+S.D. for at least 7 animals in each group. (B) ADMc1 (15 mg/kg body wt.) was administered 30 minutes before glucose load (2 g/kg body wt, i.p.). Control animals received corresponding volumes of saline. Each value represents mean±S.D. for at least 6 animals.

Figure 6:
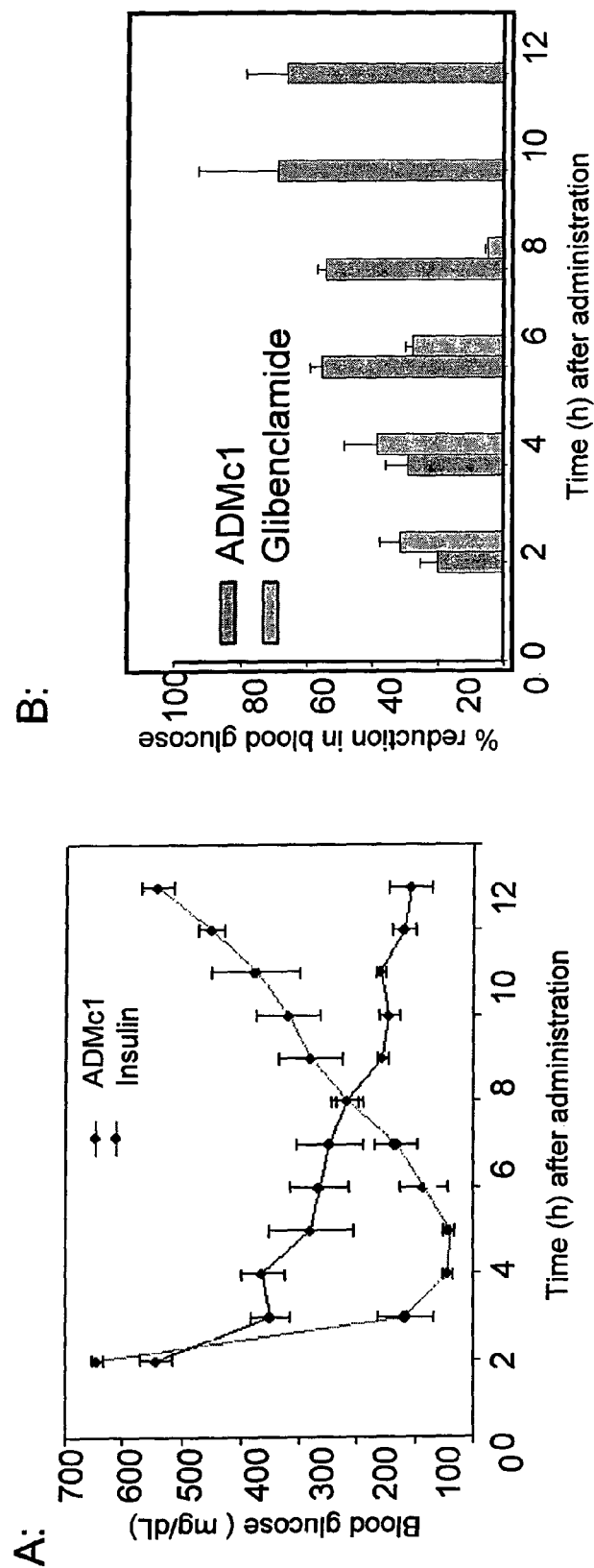

FIG. 6: Comparison of hypoglycemic/antidiabetic activity of ADMc1 in relation to known hypoglycemic/anti-hyperglycemic agents i.e. (A) Insulin and (B) glibenclamide. Diabetic animals were treated with ADMc1 (15 mg/kg body wt. each), insulin (5 μ/kg body wt.) and glibenclamide (5 mg/kg body wt.) and blood glucose was estimated at different time points. The data represent mean±S.D. for at least 7 animals in each group.

Figure 7:
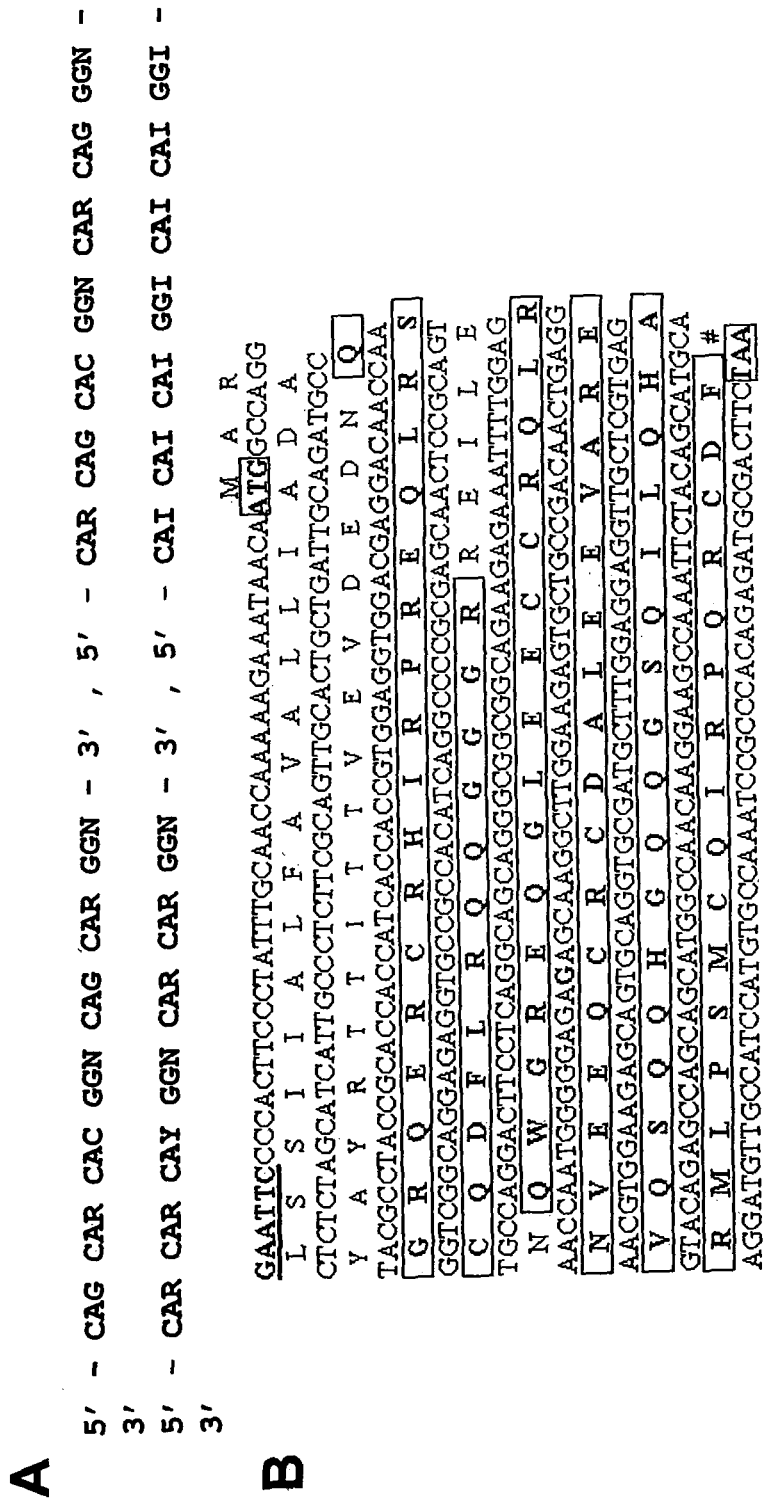

FIG. 7: (A) Oligonucleotides used for screening of the enriched cDNA library. (B) Nucleotide and deduced amino acid sequence of the isolated synthetic cDNA encoding hypoglycemic/anti-hyperglycemic protein of $M.$ $charantia$. EcoRI restriction sites at the ends, generated as a result of Ligation of the EcoRI linker are shown in bold and underlined. Initiation and termination codons are boxed. The first row shows the deduced amino acid sequence of the protein (SEQ ID NO. 5) whereas the second row shows the nucleotide sequence (SEQ ID NO. 6). The amino acid residues that constitute the mature protein are shown as boxed residues.

Figure 8:
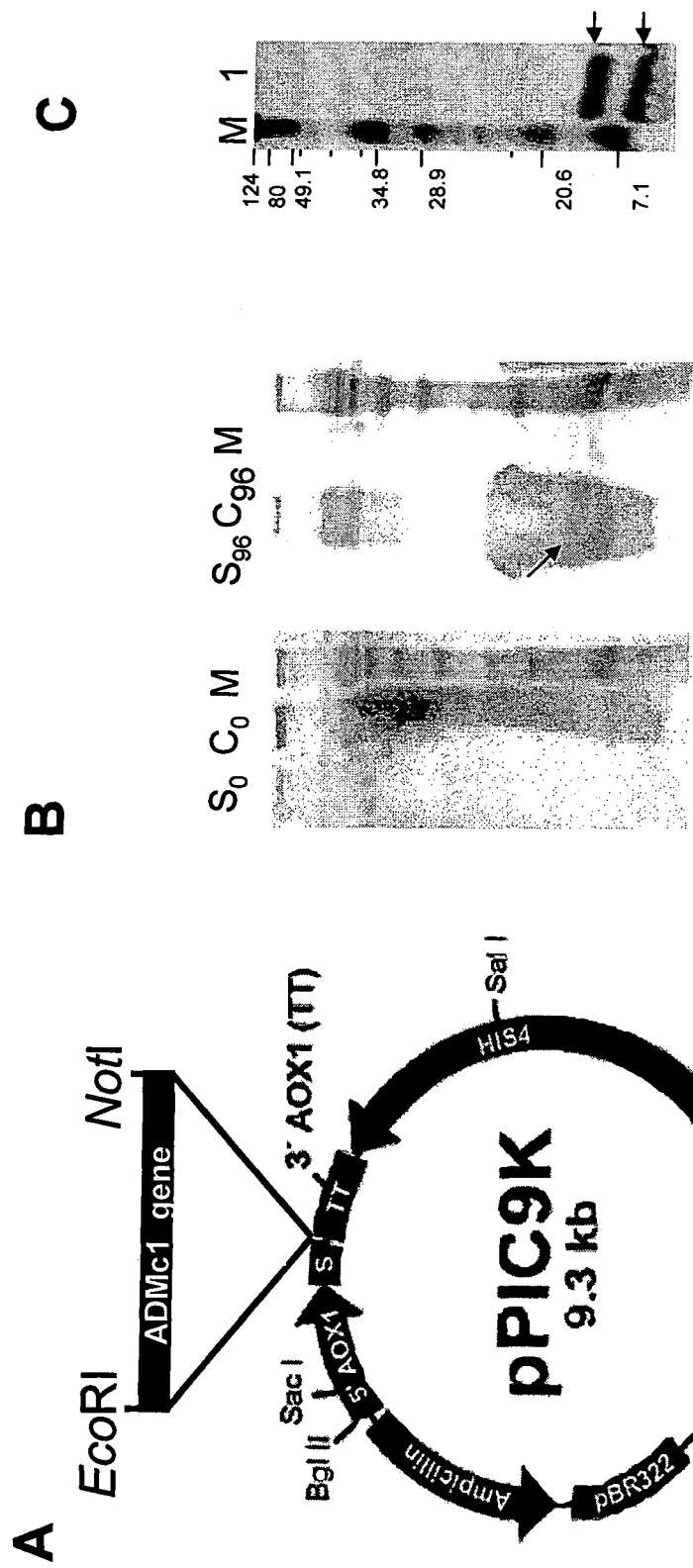

FIG. 8: (A) Schematic Map of recombinant pPIC9K plasmid harboring ADMc1 gene at EcoRI and NotI site. (B) Analysis of expression of the recombinant protein in the culture supernatant and cell lysate harvested at 0 hour and 96 hour after induction. S0 and Co=supernatant and cell lysate harvested at 0 hour, respectively. $Sg_{96}$ and $C_{96}$ culture supernatant and cell lysate harvested at 96 hour post induction, respectively. Arrow points to the expressed protein. M. indicates. protein molecular weight marker. (C) Analysis of purified recombinant protein on reducing SDS-PAGE. Like the native protein, the two polypeptides components of ADMc1 can be seen without any other contaminating protein bands.

Figure 9:
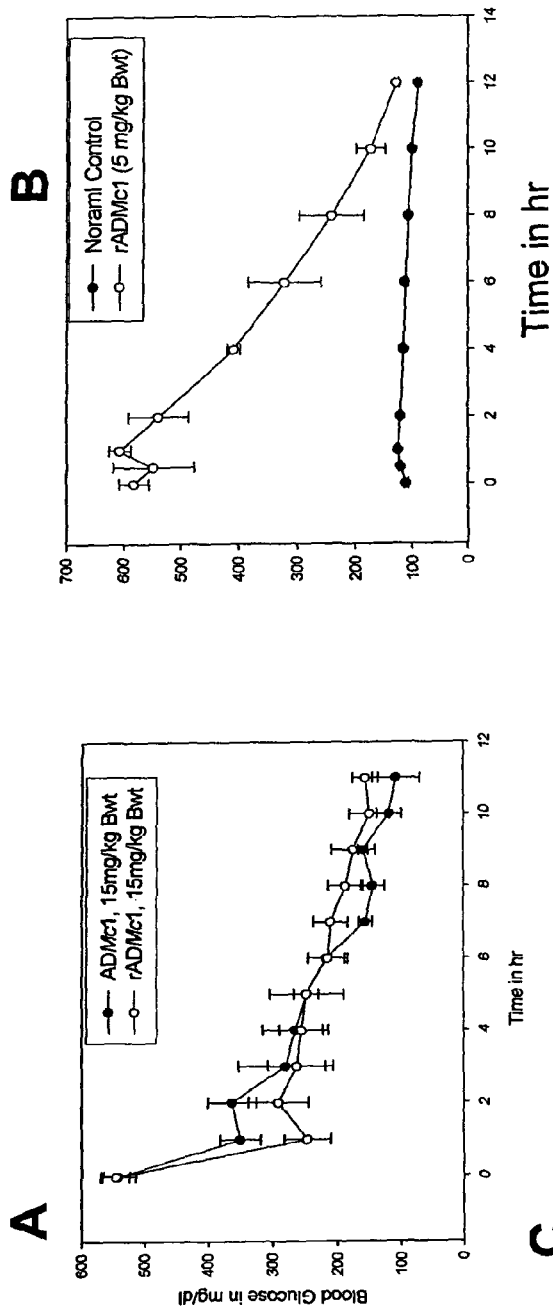
Figure 9:
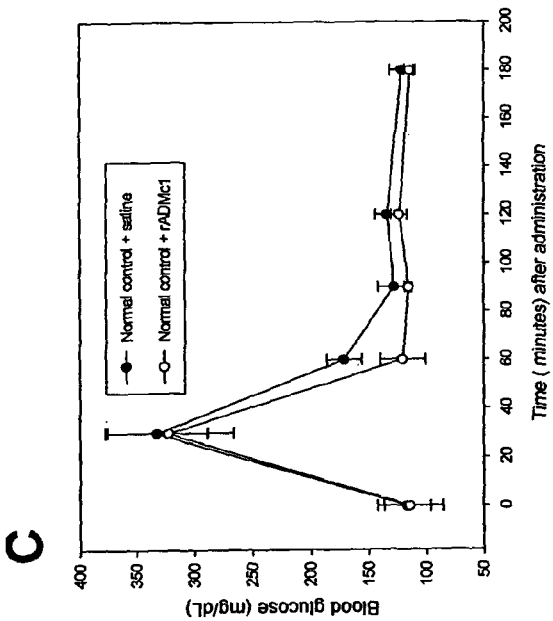

FIG. 9: Evaluation of hypoglycemic/antidiabetic activity of recombinant ADMc1 (rADMc1) A and B.: Diabetic animals are administered with native ADMc1 (purified from $M.$ $charantia$ seeds) and rADMc1 (produced in $Pichia$ $pastoris$ expression system) and blood glucose estimated at different time points. The data represent mean±S.D. for 6-7 animals in each group. C. Effect of rADMc1 (15 mg/kg B.wt.) on glucose tolerance in normal animals.

DETAILED DESCRIPTION OF THE INVENTION

The present invention discloses purified novel hypoglycemic/anti-hyperglycemic, protein from the seeds of $M.$ $charantia$. 100-125 mg of purified protein is obtained from 150 g of seeds in the present invention. Further, purification of hypoglycemic/anti-hyperglycemic molecules from the seeds of $M.$ $charantia$ is labor intensive, time consuming and costly. Availability of the seeds from $M.$ $charantia$ poses yet another limitation on the purification of the protein, as the plant is seasonal. To overcome these problems recombinant DNA route has been used in the present invention. The recombinant DNA method is a highly reproducible method free from the above mentioned limitations, to produce pure biologically active protein.

For cloning purpose, amino acid sequence of the protein is determined. Due to the blocked N-terminus of the protein, N-terminal sequencing cannot be carried out and thus amino acid sequencing of the fragments generated by tryptic digestion of the purified protein is carried out in the present invention. The sequence information of the protein thus obtained reveals it to be a novel protein.

On the basis of the sequence information of the novel sequence, radiolabeled degenerate oligonucleotides are used to screen the cDNA library made from the seeds isolated from the unripe fruits of $M.$ $charantia$. Several rounds of screening result in identification of a full length cDNA harboring the coding region of the novel anti-diabetic protein.

The region of the cDNA encoding the protein is cloned and expressed in eukaryotic expression system using methylotropic yeast $Pichia$ $pastoris$ as a host. The complete cDNA encoded for a protein of mass of 16089.8 Da. However, the mature biologically active post-translationally processed protein is of 11420.9 Da, as established by MALDI-TOF-MS. The recombinant protein is purified and its hypoglycemic/anti-hyperglycemic potential is established using experimental diabetic rat as model.

Both the cDNA sequence and the encoded protein are novel and do not match with any existing sequence both in the nucleic acid sequence database and the protein sequence database, respectively.

All the purification steps are carried out at 4° C., unless otherwise stated. Different fractions are analyzed for hypoglycemic/anti-hyperglycemic activity at each step of purification. Seeds of $M.$ $charantia$, are decorticated and powdered in liquid nitrogen. Seed proteins are extracted with a mixture of buffered sulfuric acid and ethanol (or acceptable extraction medium) containing protease inhibitor phenylmethylsulfonyl fluoride (0.5-3 mM) for 12-16 hours at −20° C. The soluble proteins are collected by centrifugation or by ultra-filtration. Proteins are further fractionated by applying a salt gradient and differential precipitation with change in pH (isoelectric) by the addition of liquid ammonia. This is subjected to further centrifugation to separate the precipitated proteins from soluble proteins. The pelleted protein and soluble protein fractions are checked for hypoglycemic/anti-hyperglycemic activity and it is established that the soluble fraction is enriched in hypoglycemic/anti-hyperglycemic activity. This fraction is then subjected to size-exclusion chromatography. Upto ~10-20 ml of the enriched fraction containing up to 150-200 mg protein is separated in one chromatographic step. Different fractions are collected and analyzed for blood glucose lowering ability in diabetic animals. The fractions showing hypoglycemic/anti-hyperglycemic activity are pooled and subjected to mass finger printing by MALDI-TOF-MS for the identification of the proteins. The sample is digested with trypsin and selected fractions are analyzed by MALDI-MS and MALDI-PSD. One of the tryptic fragments of 2160.32 Da is determined to be novel and is sequenced by Edman's degradation method. Database searches revealed it to be novel as the amino acid sequence (SEQ ID No. 1; EVQSQQHGQQGSQILQHAR) does not match with any protein in the protein sequence database.

The hypoglycemic/anti-hyperglycemic protein fraction obtained by gel filtration chromatography is further subjected to reverse-phase HPLC to purify the proteins to homogeneity. Different peak fractions are checked for hypoglycemic/anti-hyperglycemic activity. A semi-preparative analytical column is used for large scale purification of the hypoglycemic/ anti-hyperglycemic protein, and the RP-HPLC profile of the purified protein is studied. The tryptic digest of the purified protein is analyzed by LC/MS/MS followed by de novo sequencing. The amino acid sequence of one of the precursor ions matched with the novel sequence obtained earlier, thus confirming the identification of a novel hypoglycemic/anti-hyperglycemic protein. The purified protein runs as single band of ~12 kDa in non-reducing SDS-PAGE and as two bands of ~8 kDa and ~4 kDa on reducing SDS-PAGE indicating that the protein is made up of two chains linked by disulfide bridges.

The exact mass of the hypoglycemic/anti-hyperglycemic protein is determined by MALDI-TOF-MS. The purified hypoglycemic/anti-hyperglycemic protein is designated as ADMc1 (anti-diabetic protein of Momordica charantia). N-terminal sequencing can not be done, because of blocked N-terminus. The sequence of the protein is assembled by the sequence data generated from the LC/MS/MS followed by de novo sequencing of overlapping tryptic fragments.

MALDI-TOF-MS analysis reveals the exact mass of the hypoglycemic/anti-hyperglycemic protein ADMc1 and SDS-PAGE analysis, in non-reducing and reducing conditions, reveals the ADMc1 to be made up of two chains linked by disulfide bridges (SEQ ID NO. 3: QGRQERCRHIRPREQL-RSCQDFLRQQGGGR and SEQ ID NO. 4: QWGREQ-GLEECCRQLRNVEEQCRCDALE-EVAREVQSQQHGQQGSQILQHARML PSMCQIRPQRCDF). The protein is made up of 96 amino acid residues (SEQ ID NO. 2: QGRQERCRHIRPREQLR-SCQDFLRQQGGGRQWGREQGLEECCRQL-RNVEEQCR CDALEEVAREVQSQQHGQQGSQILQ-HARMLPSMCQIRPQRCDF) and its amino acid sequence reveals it to be novel that did not match with any protein in the data base. Amino acid composition analysis reveals that the protein does not contain any lysine, threonine, and tyrosine. The isoelectric point (pI) of the protein ADMc1 is calculated to be 8.15 using Gene Runner software. The protein is found to be glycosylated. The secondary structure of the ADMc1 by analysis of circular dichroism (CD) spectra, in the far-UV region, of the ADMc1 using K2d program reveals it to contain α-helix, β-sheet and random coil.

Since the recovery of the ADMc1 from seeds of M. charantia is very low, and it is cumbersome to purify the protein from plant source, it is desirable to produce the protein through recombinant DNA route. For this purpose, the cDNA encoding the ADMc1 is cloned and characterized and expressed in eukaryotic expression plasmid. The recombinant ADMc1 thus produced is purified and evaluated for its anti-diabetic activity. The procedure involved the following steps:

Total RNA is isolated from fruits bearing developing seeds of M. charantia, Poly (A)+ RNA (messenger RNA) is fractionated from total RNA using affinity chromatography. The cDNA synthesis is carried out using cDNA synthesis kit using oligo(dT) primer for the first strand synthesis and the population of the cDNA molecules ranging between 200-800 base pairs are enriched by size fractionation, followed by ligation of the EcoRI linkers to the cDNA fraction using T4 DNA ligase. The enriched cDNAs are then cloned into EcoRI-cut pBCKS+ as suggested by the vendor's protocol. The ligation mixture is transformed into Escherichia coli cells and amplified. The amplified cDNA library in E. coli cells thus obtained is pelleted, resuspended in smaller volume of medium and stored in –80° C. For screening of the cDNA encoding the hypoglycemic/anti-hyperglycemic-protein of M. charantia, a mixture of 21-.mer degenerate oligonucleotide probes are synthesized on the basis of the novel sequence of a tryptic fragment of the ADMc1 to cover all codon possibilities. Several rounds of screening of the enriched library with the radiolabeled oligonucleotides mixture is carried out till all the colonies in a plate are found to be positive. This results in a number of putative positive clones, which are then analyzed for the size of the cDNA insert by colony PCR amplification. PCR using these primers adds additional 130 base pairs in the cDNA insert. The clones showing a PCR product of greater than 600 bp are confirmed by restriction enzyme digestion using EcoRI for the release of the cDNA insert. The positive clones are subjected to automated DNA sequencing. Since the mature protein ADMc1 obtained from this cDNA is of ~12.0 kDa, it is established that the cDNA-encoded protein is a precursor of the ADMc1, which when translated in vivo gets processed to give rise the mature protein of ~12.0 kDa. Comparison of the deduced amino acid sequence from the cDNA with the amino acid sequence of the ADMc1 (assembled by sequencing of the tryptic fragments) indicates that the mature protein starts from 144th base of the cloned cDNA. It is also established that both the chains of the ADMc1 are present in one precursor polypeptide, and that other regions of the precursor are removed during post-translational processing. BlastN analysis of the nucleotide sequence of the cDNA and of the cDNA encoded protein does not show any exact match with any known gene or protein sequence in the respective databases.

For production of the hypoglycemic/anti-hyperglycemic protein through recombinant DNA technology, the gene encoding the mature protein is cloned in eukaryotic expression vectors pPIC9K. For this purpose, the cDNA region encoding the mature protein is PCR amplified by a proof reading polymerase using forward and reverse primers for cloning in the Pichia pastoris expression plasmid pPIC9K. The PCR amplified product is electrophoresed, purified and is then digested and ligated to predigested pPIC9K vector. This puts the gene encoding the hypoglycemic/anti-hyperglycemic protein of M. charantia (ADMc1) under the control of alcohol oxidase promoter and alpha mating sequence secretary signal, for efficient secretion of recombinant protein. The ligation mix is transformed and the transformants are selected, the putative positive transformants are identified by colony PCR, followed by restriction enzyme analysis and finally by automated DNA sequencing to confirm-in-frame-cloning of the ADMc1 gene. One of these positive clones is purified in large amounts for transformation of Pichia pastoris cells.

Recombinant plasmid containing ADMc1 gene is linearized with Sac I and the linearized DNA is transformed into Pichia pastoris, a histidine mutant, by electroporation as per the protocol and conditions described by the manufacturer. Positive clones are selected and putative positive clones are analyzed by colony-PCR for the presence of ADMc1 gene. Clones showing a PCR-product of the expected size are further analyzed.

Cells harboring ADMc1 clones are then selected for slow growth and normal growth on MD (Minimal dextrose) and MM (Minimal methanol) plates. Clones showing slow growth on MM plates but normal growth on MD plates are selected for further analysis for the copy-number of ADMc1 gene by growing on increasing concentrations of the antibiotic Geneticin sulphate. For this, the clones selected are patched on MD plates containing varying concentration of the drug and one of the clones that grows on maximum concentration of the antibiotic is selected for expression studies.

Expression analysis of the selected clone is and Pichia pastoris GS115 Cells harboring the recombinant construct pPIC ADMc1 are grown in buffered minimal glycerol medium (BMG) with or without yeast extract and peptone, with constant shaking till absorbance of the culture at 600 nm=4-6. The cells are then harvested by centrifugation and the supernatant is discarded and the cell palate is resuspended in ~1/10$^{th}$ volume of the initial culture volume of buffered minimal methanol medium (BMM) with or without yeast extract and peptone. The cells are further allowed to grow by incubation at 20-32° C. with constant shaking till 72 to 96 hours and 1 ml of supernatant is aliquoted every 24 hour and checked for expression. A band of ~12 kDa on non-reducing SDS-PAGE shows the expression of the recombinant protein at about 72 to 96 hours of induction. As the protein is differentially glycosylated it comes up as a diffused band.

Different conditions for maximum expression of rADMc1 are carried out at shake flask level using the protocol described earlier by varying different parameters, one at a time. For maximum expression, suitable combination of growth medium and induction medium is found to be BMG (Buffered minimal glycerol) and BMM (Buffered minimal methanol) for initial culture and induction culture, respectively. Maximum expression of the protein is obtained between 80-150 h post induction. It is established that the optimum pH suitable for proper growth of the cell and expression of the protein ranges between 5-8. Optimum temperature for proper growth and expression is found to be 25-30° C. Finally, 1% inducer concentration is found to be suitable for maximum expression. Thus, optimum conditions for maximum expression of rADMc1 are established at shake-flask level.

Recombinant ADMc1 is purified from the dialyzed culture supernatant by one-step size exclusion chromatography using Sephacryl S100 HR or Sephacryl S200 HR matrix. Pre-swollen matrix is suspended in the elution buffer and mixed gently to make a homogenous gel suspension. The gel suspension is then degassed and packed in a single step with positive pressure and is equilibrated with buffer. Upto 10-15 ml of the concentrated culture supernatant containing protein is loaded on the gel and eluted with the elution buffer. Different fractions are collected and the presence of proteins is checked by measuring the absorbance at 280 nm. Protein fractions are analyzed on SDS-PAGE. The fractions showing the presence of pure recombinant protein are pooled and concentrated and the concentrated purified protein is dialyzed in phosphate buffered saline prior to activity assay. Under optimum conditions, about 60 to 90 mg of purified protein is obtained from 1 liter of induction culture at shake flask level. Thus, the recombinant protein can be purified in a single step size-exclusion chromatography with high yield.

The present invention is applicable to all plants, plant tissues, plant cells for the isolation of the polynucleotides described in the invention.

The terms nucleic acids, polynucleotides, genes, or cDNA refer to nucleotides, either ribonucleotides, or deoxyribonucleotides or a combination of both, in a polymeric form of any length. The polynucleotides include single stranded DNA or RNA or double stranded DNA. The said terms also include all possible modifications (chemical or substitution with any other naturally occurring or synthetic nucleotide in the cDNA, DNA, mRNA, nucleic acid, polynucleotides, nucleic acid sequences, nucleotide sequence, gene or nucleic acid molecule.

The polynucleotides and the encoded polypeptide falling within the scope of the inventions can also be defined in terms of identity or similarity with that exemplified herein. The sequence identity of a sequence can be between 45 to 99% as compared to the polynucleotide sequence exemplified herein in SEQ ID NO. 5 (GAATTCCCCACTTCCCTATTTG-CAACCAAAAAGAAATAACAATGGCCAGGCT CTCTAGCATCATTGCCCTCTTCGCAGT-TGCACTGCTGATTGCAGATGCCTACG CCTACCG-CACCACCATCACCACCGTGGAGGTGGAC-GAGGACAACCAAGGTCG GCAGGAGAGGTGCCGCCACATCAGGC-CCCGCGAGCAACTCCGCAGTTGCCAG GACTTCCT-CAGGCAGCAGGGCGGCGGCAGAA-GAGAAATTTTGGAGAACCAA TGGGGGAGAGAGCAAGGCTTGGAAGAGT-GCTGCCGACAACTGAGGAACGTG GAAGAGCAGTG-CAGGTGCGATGCTTTGGAGGAGGT-TGCTCGTGAGGTACAGA GCCAGCAGCATGGCCAACAAGGAAGC-CAAATTCTACAGCATGCAAGGATGTT GCCATCCAT-GTGCCAAATCCGCCCACAGAGATGC-GACTTCTAAGCACCCTCTT AATTTTCTAGCCTACGCACTCCAAATAG-CACATTCTACCGTGCTTTTTATCTTA TGTTT-TAATAAATAAAGCCTTTAAAGAATTC) and the amino acid sequence of the protein, in part or full, as given in SEQ ID NO. 6 (MARLSSIIALFAVALLIADAYAYRTTIT-TVEVDEDNQGRQERCRHIRPREQLRSC QDFL-RQQGGGRREILENQWGREQGLEECCRQL-RNVEEQCRCDALEEVAREVQS QQHGQQGSQILQHARMLPSMCQIRPQRCDF) and that the polynucleotides are sufficiently homologous with the polynucleotide sequence as given in SEQ ID NO. 5 so as to permit hybridization of the polynucleotides sequence given in SEQ ID NO. 5 in part or full with that sequence.

Making of the said nucleic acid sequence in part or full using alternate methods such as recombinant techniques including polymerase chain reaction using specific primers, or synthetically following a chemical approach is also covered in the scope of invention.

The present invention relates to an isolated nucleic acid/polynucleotide encoding a novel plant protein having antidiabetic activity selected from either of the following: a nucleic acid sequence as given in SEQ ID NO. 5, which can be DNA, cDNA, genomic DNA or synthetic DNA or a nucleic acid comprising the RNA sequence corresponding to the nucleic acid sequence as given in SEQ ID NO. 5, a nucleic acid hybridizing to the nucleic acid given in SEQ ID NO. 5 or a nucleic acid encoding a protein with an amino acid sequence comprising the polypeptide/protein in SEQ ID NO. 6, which is homologous to the polypeptide listed in SEQ ID NO. 6 or portions thereof and exhibits 50-95% similarity to the amino acid sequence as given in SEQ ID NO. 6 and portions thereof.

Any modification or change of the nucleotides in the polynucleotide sequence as given in SEQ ID NO. 5, using the degeneracy of the codons, thus giving rise to the polypeptide as given in SEQ ID NO. 6 or portions thereof also fall within the scope of this invention.

The DNA sequences as defined in the present invention can be interrupted by intervening sequences such as introns, mobilizable DNA, insertion sequences that disrupt the coding sequences without affecting the translated product. Removal of these intervening sequences restores the coding sequence in the said expressible product.

The polynucleotides sequence as given in SEQ ID NO. 5 can be translated into 6 different frames and all the translated products fall within the scope of the present invention.

The invention also relates to the cloning of the DNA described in SEQ ID NO. 5 into an expression vector comprising regulatory sequences which allow the expression of the protein as given in SEQ ID NO. 6. A variety of specialized vectors can be used to express the said protein in a variety of hosts such as bacteria, blue green algae, plant cells, insect cells, other yeast species, or animal cells.

The invention further relates to introducing the expression vector comprising the DNA described in SEQ ID NO. 5 into suitable host and growing the host under conditions suitable for maximum expression of the desired protein.

The expression vector harbouring the gene of interest can be introduced into host cells via any one of the techniques such as transformation, transfection, protoplast fusion and is not limited to electroporation used in the present invention.

The clones of the host cells containing the expression vector are selected and analysed for their ability to express the desired protein listed in SEQ ID NO. 2 or SEQ ID NO. 6 in full or portions thereof.

The present invention is illustrated and supported by the following examples. These are merely representative examples and optimization details and are not intended to restrict the scope of the present invention in any way.

In the present invention the fragment or part of the sequence (nucleic acid or protein sequence) refers to truncated sequence of the nucleic acid and protein sequences. The truncated sequence (nucleic acid or protein sequence) can be of variable length that provides a sequence with at least a comparable function and/or activity or the original sequence referred to (e.g. "functional fragment"). While the maximum size is not critical, functional fragments also include the regions of the polypeptide/protein comprising the crucial regions of the protein for its function according to the invention.

Any of the said proteins, polypeptides, peptides and fragments thereof can be produced in a biological system, e.g. a cell culture, or chemically manufactured e.g. by solid phase peptide synthesis. Said proteins or fragments thereof can be part of a fusion protein

EXAMPLE-1

Purification of the ADMc1 from *Momordica charantia* Seeds

Seeds of *M. charantia* (Pusa Vishesh variety) obtained from Seed Sales Counter, Indian Agricultural Research Institute, Pusa Road, New Delhi, are decorticated and powdered in liquid nitrogen. Seed proteins are extracted with a mixture of buffered 0.05-0.08 M sulfuric acid and 60-80% ethanol containing protease inhibitor phenylmethylsulfonyl fluoride at a concentration of 0.5-3 mM for 12-16 hours at −20° C. The soluble proteins are collected by centrifugation at 16,000-20,000×g for 1-2 h at 4° C. or by ultrafiltration device (Amersham-Pharmacia, USA). Proteins are further fractionated by applying a salt gradient (50-80% of ammonium salts: ammonium sulfate or carbonate) or differential precipitation with change in pH (isoelectric) by the addition of liquid ammonia. The pelleted protein and soluble protein fractions are checked for hypoglycemic/anti-hyperglycemic activity and it is established that the soluble fraction is enriched in hypoglycemic/anti-hyperglycemic activity. This fraction is then subjected to size-exclusion chromatography using Sephacryl-S100 HR or Sephacryl-S200 HR matrix (Pharmacia, USA) equilibrated with 2 bed volumes of 0.05-0.25 M ammonium bicarbonate (pH 7-7.5) in a glass column of 80-100 cm (L)×2-2.5 cm (cross-sectional area). About 15-20 ml of the soluble fraction containing upto 200 mg protein is separated in one chromatographic step. The fractions showing hypoglycemic/anti-hyperglycemic activity are pooled and subjected to mass finger printing by MALDI-TOF-MS for the identification of the proteins. The sample is digested with trypsin and selected fractions are analyzed by MALDI-MS and MALDI-PSD. One of the tryptic fragments of 2160.32 Da is determined to be novel and is sequenced, by Edman's degradation method. Database searches reveal it to be novel as the amino acid sequence (SEQ ID No. 1.; EVQSQQHGQQGSQILQHAR) does not match with any protein in the protein sequence database (FIG. 1).

The hypoglycemic/anti-hyperglycemic protein fraction obtained by gel filtration chromatography is further subjected to reverse-phase HPLC (Shimadzu SCL-10A) equipped with Supelco Discovery® Bio Wide Pore, C8 analytical column (5 µm particle size, 4.6 mm×25 mm) using a linear gradient (5-90%) of acetonitrile (ACN)-trifluoro acetic acid (TFA) (Gradient solutions: 0.1% trifluoro acetic acid (TFA), V/V and 90% acetonitrile in 0.1% TFA) to purify the proteins to homogeneity. Reverse phase-HPLC purification profile of this fraction is shown in FIG. 2. Different peak fractions are checked for hypoglycemic/anti-hyperglycemic activity and the peak fraction showing the activity is marked by an arrow. A semi-preparative Supelco Discovery® Bio Wide Pore, C8 analytical column (10 µM particle size, 10 mm×250 mm) is used for large scale purification of the hypoglycemic/anti-hyperglycemic protein, and the RP-HPLC profile of the purified protein is shown in the Inset of FIG. 2. The tryptic digest of the purified protein is analyzed by LC/MS/MS followed by de novo sequencing. The amino acid sequence of one of the precursor ions of ~2159.02 matched with the novel sequence obtained earlier, thus confirming the identification of a novel hypoglycemic/anti-hyperglycemic protein. The purified protein runs as single band of ~12 kDa in non-reducing SDS-PAGE and as two bands of ~8 kDa and ~4 kDa on reducing SDS-PAGE indicating that the protein is made up of two chains linked by disulfide bridges (FIG. 4).

The exact mass of the hypoglycemic/anti-hyperglycemic protein is determined to be of 11420.9 Da by MALDI-TOF-MS. The purified hypoglycemic/anti-hyperglycemic protein is designated as ADMc1 (Anti-diabetic protein of *Momordica charantia*). The sequence of the protein is assembled by the sequence data generated from the LC/MS/MS followed by de novo sequencing of overlapping tryptic fragments.

EXAMPLE-2

Characterization of the ADMc1

MALDI-TOF MS analysis revealed the hypoglycemic/anti-hyperglycemic protein ADMc1 to be of 11420.9 Da. The protein is made up of 96 amino acid residues (SEQ ID NO. 2). SDS-PAGE analysis, in non-reducing and reducing conditions, revealed the ADMc1 to be made up of two polypeptides chains of ~4 kDa and ~8 kDa, linked by disulfide bridges. The amino acid sequence of the two polypeptide chains of ~4 kDa and ~8 kDa of ADMc1 is given in SEQ ID NO. 3 and 4, respectively. The amino acid sequence of ADMc1 revealed it to be novel that did not match with any protein in the data base. However, it showed similarity with the proteins of 2S albumin family, including conservation of 8 cysteine residues. The hetero-dimeric nature, the two polypeptide chains being linked through disulfide bridges, presence of eight conserved cysteine residues are all characteristic features of proteins of 2S albumin family of proteins. Amino acid composition analysis revealed that the protein does not contain any lysine, threonine, and tyrosine. The amino acid composition of the protein is given in Table 1. Sequence of one of the representative tryptic fragments of ADMc1 is shown in FIG. 3. The isoelectric point (pI) of the protein ADMc1 was calculated to be 8.15 using Gene Runner software. The protein was found to be glycosylated as established by Periodic acid/ Schiff staining (FIG. 4B). The secondary structure of the ADMc1 predicted by analysis of circular dichroism (CD) spectra, in the far-UV region, of the ADMc1 using K2d program (Andrade et al., 1993; Merelo et al., 1994) revealed it to contain 72% α-helix, 3% β-sheet and 25% random coil at pH 7.4.

TABLE 1

Amino acid composition of the hypoglycemic/anti-hyperglycemic protein, ADMc1

| Amino acid | Symbol | Count | % By Number | % By Wt |
|---|---|---|---|---|
| Ala | A | 3 | 3.12 | 2.34 |
| Arg | R | 16 | 16.67 | 24.40 |
| Asn | N | 1 | 1.04 | 1.16 |
| Asp | D | 3 | 3.12 | 3.50 |
| Cys | C | 8 | 8.33 | 8.48 |
| Glu | E | 10 | 10.42 | 12.88 |
| Gln | Q | 19 | 19.79 | 24.31 |
| Gly | G | 8 | 8.33 | 5.26 |
| His | H | 3 | 3.12 | 4.08 |
| Ile | I | 3 | 3.12 | 3.45 |
| Leu | L | 7 | 7.29 | 8.04 |
| Lys | K | 0 | 0.00 | 0.00 |
| Met | M | 2 | 2.08 | 2.61 |
| Phe | F | 2 | 2.08 | 2.89 |
| Pro | P | 3 | 3.12 | 3.02 |
| Ser | S | 4 | 4.17 | 3.68 |
| Thr | T | 0 | 0.00 | 0.00 |
| Trp | W | 1 | 1.04 | 1.79 |
| Tyr | Y | 0 | 0.00 | 0.00 |
| Val | V | 3 | 3.12 | 3.08 |

EXAMPLE-3

Demonstration of Hypoglycemic/Anti-Hyperglycemic Activity of ADMc1

To check the bioactivity of the purified ADMc1, alloxan-diabetic rats are used. For this purpose, alloxan monohydrate (freshly prepared in 0.154 M sodium acetate buffer, pH 4.5; 15 mg/100 g body weight) is administered intraperitoneally to male wistar rats that are starved for 36 hrs. Control rats are injected with corresponding volumes of sodium acetate buffer. They are fed ad libitum and plenty of water is provided. For initial 3 days, rats are administered 2 units of lent insulin intraperitoneally for stabilization, following which, blood glucose level is estimated and animals having glucose level more than 400 mg/100 ml blood are tested with the purified native ADMc1 along with other known hypoglycemic/anti-hyperglycemic agents. Native ADMc1 (purified from the seeds) is administered subcutaneously at a dose of 15 mg/kg body weight. After administration of the test protein, blood is withdrawn retro-orbitally at 0 hr and then upto 12 hours, on hourly basis. Glucose level is estimated immediately after bleeding using glucose estimation kit (Merkotest, of Merck, Germany). Percent lowering of blood glucose is calculated using the formulae, % Lowering=$\{(Glu_0-Glu_t)/Glu_0\} \times 100$, where in $Glu_0$=Glucose concentration at 0 hr. $Glu_t$=Glucose concentration at time "t".

Blood glucose lowering activity of the ADMc1 is shown in FIG. 5A. It is evident that the purified ADMc1 lowers the blood glucose levels significantly. The ADMc1 also increases glucose tolerance in normal test animals, but not significantly, thus suggesting that the ADMc1 is anti-hyperglycemic in action (FIG. 5B). The reduction in the blood glucose levels brought about by ADMc1 is comparable with that brought about by insulin (FIG. 6A) and is found to be more effective than known glibenclamide which reduces the blood glucose levels by 39% in 4 h (FIG. 6B). Purified ADMc1 reduces the blood glucose levels by 70%. Glibenclamide does not show any significant reduction in the glucose levels beyond this point. Unlike insulin that needs to be administered before every meal, the ADMc1 maintains the lower blood glucose level for longer periods and needs to be administered only once a day. It is important to note that ADMc1 brings down the glucose levels slowly and maintains them for longer period. Thus, there is no risk of sudden hypoglycemia, which is often the case with other known hypoglycemic/anti-hyperglycemic agents such as insulin.

EXAMPLE-4

Construction of Partial cDNA Library from *M. charantia* Seeds

Total RNA is isolated from unripe fruits bearing developing seeds of *M. charantia* (Pusa Vishesh variety) using Trizol reagent from Sigma Chemical company, USA as per the manufacturer's instructions. Poly (A)+ RNA (messenger RNA) is fractionated from total RNA using oligo dT-agarose affinity chromatography (Oligo-dT agarose, New England Biolabs, USA). The cDNA synthesis is carried out using cDNA synthesis kit (Promega, Cat. No. C4360) using oligo (dT) primer for the first strand synthesis and the population of the cDNA molecules ranging between 200-800 base pairs are enriched by size fractionation, followed by ligation of the EcoRI linkers (Promega, USA) to the cDNA fraction using T4 DNA ligase (New England Biolabs, USA). The enriched cDNAs are then cloned into EcoRI digested, calf alkaline phosphatase treated pBCKS+ plasmid as suggested by the vendor's protocol. The ligation mixture is transformed into Esherichia coli DH5α cells and amplified in the Luria-Bertani broth containing chloramphenicol (30 µg/ml). The amplified cDNA library in *E. coli* cells thus obtained is pelleted, resuspended in smaller volume of medium with 20% glycerol as described by Sambrook et al. (1989) and stored in −80° C.

For screening of the cDNA clone encoding the hypoglycemic/anti-hyperglycemic protein of *M. charantia*, a mixture of 21-mer degenerate oligonucleotide probes are synthesized on the basis of the novel sequence of a tryptic fragment (2160.32 Da) of the ADMc1 to cover all codon possibilities. The sequence of the oligonucleotide used for screening the library is given in FIG. 7A. Several rounds of screening of the enriched library with the radiolabeled oligonucleotides mixture is carried out till all the colonies in a plate are found to be positive. This results in a number of putative positive clones, which are then analyzed for the size of the cDNA insert by colony PCR amplification using T7 and T3 primers present in the plasmid vector. PCR using these primers adds additional 130 base pairs in the cDNA insert. The clones showing a PCR product of greater than 600 bp, are confirmed by restriction enzyme digestion using EcoRI for the release of the cDNA insert. The positive clones are subjected to automated DNA sequencing. Analysis of the sequence of these clones reveal that one of the clones consisting of a 541 bp cDNA insert show the presence of a single open reading frame encoding a protein of ~16 kDa (made up of 138 amino acid residues) with translation initiation codon, termination codon and 3' untranslated region. The nucleotide sequence and the deduced amino acid sequence of the protein is shown in FIG. 7B. This clone is designed as pBCKS-ADMc1 (plasmid encoding *M. charantia* hypoglycemic/anti-hyperglycemic protein). Since the mature protein ADMc1 obtained from this cDNA is of 11.420 kDa, it is established that the cDNA-encoded protein is a precursor of the ADMc1, which when translated in vivo gets processed to give rise the mature protein of ~11.420 kDa. Comparison of the deduced amino acid sequence from the cDNA with the amino acid sequence of the ADMc1 (assembled by sequencing of the tryptic fragments) indicates that the mature protein starts from $144^{th}$ base of the cloned cDNA. It is also established that both the chains of the ADMc1 are present in one precursor polypeptide, and that other regions of the precursor are removed during post-translational processing. BlastN analysis (NCBI server) of the nucleotide sequence of the cDNA and the BlastP analysis (NCBI server) of the cDNA encoded protein does not show any exact match with any known gene or protein sequence in the respective databases.

EXAMPLE-5

Cloning of ADMc1 Gene in Pichia Expression Vector pPIC9K

The gene encoding the mature protein is cloned in eukaryotic expression vectors pPIC9K as per the direction of the manufacturer. For this purpose, the cDNA region encoding the mature protein (starting from the $144^{th}$ base of the cloned cDNA to the termination codon) is PCR amplified from pBCKS-ADMc1 by a proof reading polymerase (Vent DNA polymerase from New England Biolabs, USA) using forward and reverse primers consisting of EcoRI and NotI sites, respectively, for convenient cloning in the Pichia pastoris expression plasmid pPIC9K. The PCR amplified product is electrophoresed in 1.2% low melting agarose gel and purified by ethanol precipitation. This is then digested with EcoRI and NotI (New England Biolabs, USA) and ligated to pPIC9K vector predigested with EcoRI and NotI. This puts the gene encoding the hypoglycemic/anti-hyperglycemic protein of M. charantia (ADMc1) under the control of alcohol oxidase I (AoxI) promoter and alpha mating sequence secretary signal, for efficient secretion of recombinant protein. The ligation mix is transformed into E. coli DH5α and the transformants are selected on LB-agar plates containing ampicillin. The putative positive transformants are identified by colony PCR followed by restriction enzyme analysis and finally by automated DNA sequencing to confirm in frame cloning of the ADMc1 gene. One of these positive clones, designated as pPIC-ADMc1, has mature ADMc1 cDNA under the control of Aox1 promoter. The schematic map of final construct, i.e. recombinant plasmid pPIC9K harboring ADMc1 gene is shown in FIG. 8A. Plasmid pPIC-ADMc1 DNA is purified in large amounts for transformation of Pichia pastoris cells.

Recombinant plasmid containing ADMc1 gene (pPIC-ADMc1) is linearized with) Sac I and the linearized DNA is transformed to GS115 strain of Pichia pastoris (Invitrogen, USA), a histidine mutant, by electroporation as per the protocol and conditions described by the manufacturer (Invitrogen, USA). Positive clones are selected on minimal dextrose (MD) plate. Putative positive clones are analyzed by colony-PCR for the presence of ADMc1 gene using primer specific for ADMc1 gene. Clones showing a PCR-product of the expected size are further analyzed. GS115 cells harboring ADMc1 clones are then selected for Mut$^s$ (Slow growth on methanol carbon source) and Mut$^+$ (Normal growth on Methanol carbon source) phenotype on MD (Minimal dextrose) and MM (Minimal methanol) plates as described by the manufacturer (Invitrogen, USA). Clones showing slow growth on MM plates but normal growth on MD plates are selected for further analysis for the copy-number of ADMc1 gene by growing on increasing concentrations of the antibiotic G418 (Geneticin sulphate, Sigma Chemical Co., USA). For this, the clones selected as Mut$^s$ are patched on MD plates containing varying concentration of the drug and one of the clones that grows on maximum concentration of G418 is selected for expression studies.

Expression analysis of the selected clone is performed as per the instruction of Pichia expression kit, (Invitrogen, USA). Pichia pastoris GS115 cells harboring the said recombinant construct pPIC-ADMc1 are grown in buffered minimal glycerol medium (BMG) with or without yeast extract and peptone, between 20-32° C. with constant shaking till absorbance of the culture at 600 nm=4-6. The cells are then harvested by centrifugation at 8000 rpm for 20 min at 4° C. (SS34 rotor, Sorvall, USA). The supernatant is discarded and the cell palate is resuspended in $\sim\frac{1}{10}^{th}$ volume of the initial culture volume of buffered minimal methanol medium (BMM) with or without yeast extract and peptone. The cells are further allowed to grow by incubation at 20-32° C. with constant shaking till 96 hours and 1 ml of supernatant is aliquoted every 24 hour and checked for expression. A band of ~12 kDa on non-reducing SDS-PAGE shows the expression of recombinant protein (FIG. 8B) at about 96 h of induction.

To find out optimum time of induction, culture is grown as described earlier and incubated till 240 hours with periodic induction by 0.04% to 0.06% methanol every 24 hour and aliquots are taken for analysis every 24 hours before induction. After 240 hours of incubation the volume of culture supernatant aliquot is reduced to $\frac{1}{10}^{th}$ of the original. The expression of the rADMc1 is analyzed by SDS-PAGE. Maximum expression of the recombinant protein occurs between 80-150 hours post induction.

EXAMPLE-6

Purification of the Recombinant Hypoglycemic/Anti-Hyperglycemic Protein of M. charantia (rADMc1)

Recombinant ADMc1 is purified from the dialyzed culture supernatant by one-step size exclusion chromatography using Sephacryl S100 HR or, Sephacryl S200 HR matrix (Pharmacia, USA). The column used for this purpose has the dimension, 80 cm (length)×2.50 (cross sectional area), fitted with a frit of sintered glass of pore size, 90-150 µm. Pre-swollen matrix (300 ml) is suspended in 400 ml of the elution buffer [0.2 M $(NH_4)_2HCO_3$, pH 7.2-7.4] and mixed gently to make a homogenous suspension. The gel suspension is then degassed and packed in a single step with positive pressure, with the flow rate of 15-20 ml/h. It is equilibrated with 3 bed volumes of buffer. Void volume (Vo) of the column is calculated using blue dextran (2000 kDa). Upto 10-15 ml of the sample (concentrated culture supernatant) containing ~200 mg protein is loaded on the gel using a 3-way valve and eluted with the elution buffer at a flow rate of 15-18 ml/h. Different fractions (4.5 ml each) are collected and the presence of proteins is checked by measuring the absorbance at 280 nm. Protein fractions are analyzed on 16.5% SDS-PAGE. The fractions showing the presence of pure recombinant protein are pooled and concentrated by ultra-filtration device (Amersham-Pharmacia, USA) or by lyophilization in lyophilizer (Labconco, USA). SDS-PAGE analysis of purified protein is shown in FIG. 8C. The protein is greater than 98% pure as established by densitometric scanning of the SDS-PAGE. The concentrated purified protein is dialyzed in phosphate buffered saline prior to activity assay. Under optimum conditions, about 70 mg of purified protein could be obtained from 1 liter of induction culture at shake flask level. Thus, the recombinant protein can be purified in a single step size-exclusion chromatography with high yield.

EXAMPLE-7

Bioactivity of the rADMc1

The bioactivity of the rADMc1 is checked in experimental Alloxan-diabetic rats, as described earlier with native ADMc1. Native ADMc1 (purified from *M. charantia* seeds) and the recombinant ADMc1 (produced in *Pichia pastoris*) are administered subcutaneously at a dose of 15 mg/kg body weight. Blood is withdrawn retro-orbitally at 0 hr and then every hour for 10-12 hours, and blood glucose is estimated immediately using glucose estimation kit (Merkotest, of Merck, Germany). It is found that the recombinant protein is active during the observation period and is as effective as the native protein (FIG. 9A). Even at a lower dose (5 mg/kg body weight, the recombinant protein is equally effective (FIG. 9B). Approximately, ~70% reduction in the blood glucose levels of diabetic animals is brought by $11^{th}$ hour. Both the native ADMc1 and the rADMc1 exhibit better hypoglycemic/anti-hyperglycemic activity than the positive control, insulin, as the glucose lowering effect lasts longer than insulin. The test subjects do not undergo sudden hypoglycemia as the lowering of glucose is slower. Like the native protein, no significant change in the glucose tolerance is observed in the normal animals treated with recombinant protein as well (FIG. 9C), confirming its anti-hyperglycemic action. A single injection of the ADMc1 and rADMc1 is given in the morning to the diabetic animals and the blood is withdrawn every two hours for 24 hours. Both the ADMc1 and the rADMc1 are able to maintain the blood glucose levels of the diabetic animals for the whole day and the animals need only single injection per day. The experimental diabetic animals are thus maintained on the rADMc1 (i.e. 15 mg/kg body weight, everyday) for over 3 weeks with no visible side effects.

Effect of daily administration (subcutaneous administration.) of rADMc1 for 3 weeks on liver and kidney functions and on local tissue at the site of administration is evaluated. Serum is collected at the end of the experimental period and analyzed for various biochemical parameters for liver and kidney function. Skin biopsies are collected from the site of administration and histological condition checked. No acute toxicity is observed with rADMc1 as established by the analysis of various parameters for liver and kidney functions. For liver function, the marker enzymes serum glutamate oxaloacetate transaminase (SGOT), serum glutamate pyruvate transaminase (SGPT) and alkaline phosphatase (ALP) are measured in the serum of treated animals. No rise in the activities of these enzymes are observed when compared to control animals (treated with saline), indicating that there is no liver damage. Similarly, no electrolyte imbalance and changes in the urea and creatinine levels are observed in the animals treated with rADMc1, suggesting no toxic effect on kidney. The histopathology of the skin tissue at the site of administration confirmed that the tissue harvested from rADMc1-treated animals did not show any deviation from that of the normal controls. No signs of vasculitis, necrosis, inflammatory infiltration and foreign body granulomas is observed in the rADMc1-treated animals indicating that rADMc1 does not cause any local toxicity. Even the basal blood glucose levels in rADMc1-treated animals comes down much lower.

The present invention is of significance as the numbers of diabetic patients are increasing world-wide and India has the fastest growing population of diabetics. The economic impact of diabetes is enormous and the problem needs to be addressed on urgent basis by identifying the effective therapeutic agents without any side-effects.

The present invention describes identification of a highly effective, plant derived protein with anti-diabetic/anti-hyperglycemic activity, which will be of immense use in the treatment of diabetes as it needs to be administered only once a day. Thus, the present invention meets the desired goal of controlling blood sugar levels on a 24 h basis for the management of diabetes mellitus. Further, the same protein is expressed in an expression system, acceptable for human use. The recombinant protein production gives higher yields of the recombinant protein which is as effective as the native protein purified from the seeds of *M. charantia*. Unlike the proteins purified from the plant source, where the quality and the yield of the protein depends upon the environment from where the plant tissue is harvested, production of the ADMc1 through recombinant protein gives consistent preparations.

It is to be understood that the structure of the present invention is susceptible to modifications, changes and adaptations by those skilled in the art. Such modifications, changes and adaptations such as isotypes, isoforms or derivatives of the novel hypoglycemic/anti-hyperglycemic protein or production of derivatives of the novel cDNA encoding novel hypoglycemic/anti-hyperglycemic protein by splicing, fragmenting or modifying the cDNA or linking the whole cDNA or the portions thereof with another carrier protein gene thereby modifying the recombinant protein produced thereof, are intended to be within the scope of the present invention.

Substitutional/deletion or insertion variants of the protein of the present invention or its fragment/part are intended to be covered in this invention.

Substitutional variants (single or clustered) are those polypeptides in which one or more amino acid residue in said protein amino acid sequence has been removed and replaced by inserting a different residue or more than one residues in its place. Deletional variants of a protein of the invention are characterized by the removal of one or more amino acids from the amino acid sequence of said protein from any where in the protein i.e. from the amino or carboxy terminal ends or from within the polypeptide of the invention.

Insertional amino acid sequence variants of the protein of the invention are the polypeptides in which one or more amino acid residues are introduced into the said protein such as at the amino-terminal and/or carboxy-terminal fusions as well as intra-sequence insertions of single or multiple amino acids.

All such variants or homologues, described above, can be produced using synthetic procedures well known in the art such as recombinant DNA manipulations or solid phase peptide synthesis etc.

Any manipulation of the DNA sequence of the present invention to produce variant proteins which manifest as substitutional, insertional or deletional variants falls within the scope of this invention. Such manipulations are well known in the art and can be introduced by using various tools and kits available commercially or generated in house. These include PCR-mediated site directed mutagenesis or any other site-directed mutagenesis protocols.

Difference Between ADMc1 and Polypeptide-p and Polypeptide-k:
1) ADMc1 is made up of 96 amino acid residues whereas, earlier reported proteins polypeptide-p and polypeptide-k are of 166 and 160 amino acid residues, respectively.
2) ADMc1 is water-soluble while polypeptide-p is partially water-soluble and polypeptide-k is soluble in 10% formic acid.
3) ADMc1 has cyclized blocked N-terminal, while the polypeptide-k has free N-terminal.
4) ADMc1 is a well-defined protein with characterized amino-acid sequence, pI and secondary structure, while the polypeptide-p and polypeptide-k lack the amino-acid sequence and molecular structure characterization, thus making these ambiguous.
5) ADMc1 maintains the blood glucose level of experimental diabetic rats for 24 hours whereas the polypeptide-p and polypeptide-k requires multiple doses in subjects to maintain the blood glucose level.

Advantages of Recombinant Hypoglycemic/Anti-Hyperglycemic Protein (rADMc1)
1) The rADMc1 is a highly defined preparation of a highly effective protein produced in a controlled environment, thus consistency of the product is maintained.
2) The production of the hypoglycemic/anti-hyperglycemic protein of *Momordica charantia* (ADMc1) using recombinant DNA technology eliminates the requirement of plant source as raw material.
3) Production of the recombinant protein does not have the limitation of purification of the proteins from the plant source, which depends upon the availability of the plant source.
4) Production of recombinant hypoglycemic/anti-hyperglycemic protein ADMc1 is much easier as the gene is cloned and requires only culturing of the clones of *Pichia pastoris* cells harboring the gene for the same, whereas purification of proteins from any plant source, including seeds is cumbersome, time-consuming and requires the use of a variety of chemical reagents.
5) As the rADMc1 is expressed in *Pichia pastoris*, an eukaryotic expression system, the protein thus obtained is properly folded with all the post-translation modification and closest to native protein.
6) Proteins expressed in *Pichia pastoris* are approved for human use. Thus, the recombinant hypoglycemic/anti-hyperglycemic protein, ADMc1 produced in *Pichia pastoris* is acceptable for human use.
7) As the rADMc1 is expressed as secretory protein and purified from the medium thus eliminating the risk of contamination of any *Pichia* protein, while the proteins purified from the seed source always have a risk of contamination from soil of pesticides and insecticides.
8) Purification of rADMc1 is a simple one-step gel chromatography process and is therefore cost effective while extraction from seeds requires fractionation using various organic solvents followed by two or three purification processes.
9) The rADMc1 can be produced in any part of the world at any time of the year and does not pose any limitations associated with the availability of the plant material.
10) A high (70 mg/liter of culture) and consistent yield of a defined protein is obtained in case of rADMc1, while poor and inconsistent yields are obtained from seed extraction due to human error and plant source.
(11) The rADMc1 is water-soluble while the previously identified principles are water-insoluble.
12) The rADMc1 does not show any cross reactivity with insulin antibodies.
13) A single dose of the rADMc1 is sufficient to bring down the blood glucose levels by 50-80% of the experimental diabetic rats and maintain the reduced blood glucose level of experimental diabetic rats for upto 24 hrs while the previously identified principles require multiple doses to maintain the blood glucose level in normal range.

The invention claimed is:

1. A hypoglycemic/anti-hyperglycemic protein comprising ADMc1 purified from seeds of *Momordica charantia* consisting of SEQ ID NO:2.

2. A composition as claimed in claim 1, consisting of hypoglycemic/anti-hyperglycemic protein consisting of SEQ ID NO:2 and one or more excipients, vehicles, additives, adjuvants or modulators.

3. A hypoglycemic/anti-hyperglycemic protein consisting of two chains of ~4 kDa consisting of SEQ ID NO:3 and ~8 kDa consisting of SEQ ID NO:4.

4. A composition comprising a hypoglycemic/anti-hyperglycemic protein, wherein said hypoglycemic/anti-hyperglycemic protein comprises ADMc 1 or recombinant ADMc 1 wherein said ADMc 1 or recombinant ADMc 1 comprises residues 37 to 66 and 73 to 138 of SEQ ID NO: 6.

5. A cDNA consisting of SEQ ID NO:5 encoding hypoglycemic/antihyperglycemic protein ADMc 1 of *Momordica charantia*.

6. A process for the purification of hypoglycemic/anti-hyperglycemic protein ADMc 1 consisting of SEQ ID NO: 2 purified from seeds of *Momordica charantia* comprising the steps of:
   a) decorticating and powdering said seeds;
   b) extracting seed proteins from the decorticated and powdered seeds obtained from step (a);
   c) fractionating said seed proteins;
   d) separating a soluble protein fraction and pelleted proteins wherein the soluble protein fraction is enriched in hypoglycemic/anti-hyperglycemic protein ADMc 1 consisting of SEQ ID NO: 2; and
   e) purifying the protein fraction enriched in hypoglycemic/anti-hyperglycemic activity to homogeneity.

7. The process as claimed in claim 6, wherein performing said decorticating and powdering of step a) occurs in liquid nitrogen.

8. The process as claimed in claim 6, wherein performing said extracting seed proteins of step b) via a mixture of buffered sulfuric acid ethanol or other acceptable extraction medium, containing protease inhibitor phenylmethylsulfonyl fluoride.

9. The process as claimed in claim 8, wherein said phenylmethylsulfonyl fluoride is 0.5-3 mM.

10. The process for the purification of hypoglycemic/anti-hyperglycemic protein as claimed in claim 6, wherein performing said fractioning of step c) via centrifuging at 16,000-20,000×g for 1-2 h at 4°, by ultrafiltration, by salt or pH gradient or a combination thereof.

11. The process for the purification of hypoglycemic/anti-hyperglycemic protein as claimed in claim 6, wherein performing said purifying said protein fraction enriched in hypoglycemic/anti-hyperglycemic protein ADMc1 consisting of SEQ ID NO:2 of step e) via subjecting the soluble protein fraction to reverse-phase HPLC.

12. A process for preparation and purification of recombinant hypoglycemic/anti-hyperglycemic protein rADMc1 purified from seeds of *Momordica charantia* comprising the steps of:
   (i) isolating and purifying mRNA from unripe fruits bearing developing seeds of *M. charantia;*
   (ii) preparing cDNA from said purified mRNA;
   (iii) isolating the cDNA of SEQ ID NO:5 from cDNA prepared in step (ii) encoding said hypoglycemic/anti-hyperglycemic protein;
   (iv) cloning the isolated cDNA consisting of SEQ ID NO:5 encoding said hypoglycemic/anti-hyperglycemic protein into an expression vector;
   (v) isolating cDNA consisting of SEQ ID NO:5 encoding said hypoglycemic/anti-hyperglycemic protein;
   (vi) transforming *Pichia pastoris* with said cDNA of step (v);
   (vii) cultivating *Pichia pastoris* containing said hypoglycemic/anti-hyperglycemic protein clone wherein said hypoglycemic/anti-hyperglycemic protein clone is cultivated by culturing said *Pichia pastoris* in culture medium to produce recombinant hypoglycemic/anti-hyperglycemic protein rADMc1; and (viii) purifying said recombinant hypoglycemic/anti-hyperglycemic protein from said culture medium.

13. The process as claimed in claim 12, wherein said *Pichia pastoris* is *Pichia pastoris* GS115.

14. The process as claimed in claim 12, wherein said expression vector is pPIC9K.

15. The process as claimed in claim 12, wherein said culture medium is a combination of growth culture medium and induction culture medium.

16. The process as claimed in claim 15, wherein said growth culture medium is buffered minimal glycerol (BMG) medium.

17. The process as claimed in claim 15, wherein said induction culture medium is buffered minimal methanol (BMM) medium.

18. The process as claimed in claim 12, wherein said purifying of step (viii) occurs by one-step size exclusion chromatography.

19. The process as claimed in claim 12, comprising obtaining from one liter of induction culture about 70 mg of purified protein.

20. A method of treating a mammal suffering from hyperglycemia which comprises administering to said mammal hypoglycemic/anti-hyperglycemic protein consisting of SEQ ID NO: 2 or recombinant ADMc 1 comprising residues 37 to 66 and 73 to 138 of SEQ ID NO: 6, or a pharmaceutical composition comprising said hypoglycemic/anti-hyperglycemic protein consisting of SEQ ID NO: 2 or recombinant ADMc 1 comprising residues 37 to 66 and 73 to 138 of SEQ ID NO: 6.

21. The method as claimed in claim 20, wherein said mammal is a human.

22. The method as claimed in claim 20, wherein administering is via a single dose of said hypoglycemic/anti-hyperglycemic protein so as to reduce the blood glucose levels of a diabetic subject by 50-80% and maintains the lower blood glucose level for up to 24 hrs.

23. The method as claimed in claim 20, wherein the single dose of 5 to 15 mg/kg body weight per day does not show any toxic side effect in the mammal.

\* \* \* \* \*

SEQUENCE LISTING

```
<160> NUMBER OF SEQ ID NOS: 6

<210> SEQ ID NO 1
<211> LENGTH: 19
<212> TYPE: PRT
<213> ORGANISM: Momordica charantia

<400> SEQUENCE: 1

Glu Val Gln Ser Gln Gln His Gly Gln Gln Gly Ser Gln Ile Leu Gln
1               5                   10                  15

His Ala Arg

<210> SEQ ID NO 2
<211> LENGTH: 96
<212> TYPE: PRT
<213> ORGANISM: Momordica charantia

<400> SEQUENCE: 2

Gln Gly Arg Gln Glu Arg Cys Arg His Ile Arg Pro Arg Glu Gln Leu
1               5                   10                  15

Arg Ser Cys Gln Asp Phe Leu Arg Gln Gln Gly Gly Gly Arg Gln Trp
            20                  25                  30

Gly Arg Glu Gln Gly Leu Glu Glu Cys Cys Arg Gln Leu Arg Asn Val
```

```
                35                  40                  45
Glu Glu Gln Cys Arg Cys Asp Ala Leu Glu Val Ala Arg Glu Val
 50                  55                  60

Gln Ser Gln Gln His Gly Gln Gly Ser Gln Ile Leu Gln His Ala
 65                  70                  75                  80

Arg Met Leu Pro Ser Met Cys Gln Ile Arg Pro Gln Cys Asp Phe
                 85                  90                  95

<210> SEQ ID NO 3
<211> LENGTH: 30
<212> TYPE: PRT
<213> ORGANISM: Momordica charantia

<400> SEQUENCE: 3

Gln Gly Arg Gln Glu Arg Cys Arg His Ile Arg Pro Arg Glu Gln Leu
 1               5                   10                  15

Arg Ser Cys Gln Asp Phe Leu Arg Gln Gln Gly Gly Gly Arg
             20                  25                  30

<210> SEQ ID NO 4
<211> LENGTH: 66
<212> TYPE: PRT
<213> ORGANISM: Momordica charantia

<400> SEQUENCE: 4

Gln Trp Gly Arg Glu Gln Gly Leu Glu Glu Cys Cys Arg Gln Leu Arg
 1               5                   10                  15

Asn Val Glu Glu Gln Cys Arg Cys Asp Ala Leu Glu Glu Val Ala Arg
             20                  25                  30

Glu Val Gln Ser Gln Gln His Gly Gln Gln Gly Ser Gln Ile Leu Gln
         35                  40                  45

His Ala Arg Met Leu Pro Ser Met Cys Gln Ile Arg Pro Gln Arg Cys
     50                  55                  60

Asp Phe
 65

<210> SEQ ID NO 5
<211> LENGTH: 553
<212> TYPE: DNA
<213> ORGANISM: Momordica charantia

<400> SEQUENCE: 5
gaattcccca cttccctatt tgcaaccaaa agaaataac  aatggccagg ctctctagca     60
tcattgccct cttcgcagtt gcactgctga ttgcagatgc ctacgcctac cgcaccacca    120
tcaccaccgt ggaggtggac gaggacaacc aaggtcggca ggagaggtgc cgccacatca    180
ggccccgcga gcaactccgc agttgccagg acttcctcag gcagcagggc ggcggcagaa    240
gagaaatttt ggagaaccaa tggggggagag agcaaggctt ggaagagtgc tgccgacaac    300
tgaggaacgt ggagagcag tgcaggtgcg atgctttgga ggaggttgct cgtgaggtac    360
agagccagca gcatggccaa caaggaagcc aaattctaca gcatgcaagg atgttgccat    420
ccatgtgcca atccgcccca cagagatgcg acttctaagc accctcttaa ttttctagcc    480
tacgcactcc aaatagcaca ttctaccgtg cttttatct tatgttttaa taaataaagc    540
ctttaaagaa ttc                                                       553

<210> SEQ ID NO 6
<211> LENGTH: 138
<212> TYPE: PRT
```

```
<213> ORGANISM: Momordica charantia

<400> SEQUENCE: 6

Met Ala Arg Leu Ser Ser Ile Ile Ala Leu Phe Ala Val Ala Leu Leu
 1               5                  10                  15

Ile Ala Asp Ala Tyr Ala Tyr Arg Thr Thr Ile Thr Thr Val Glu Val
             20                  25                  30

Asp Glu Asp Asn Gln Gly Arg Gln Glu Arg Cys Arg His Ile Arg Pro
         35                  40                  45

Arg Glu Gln Leu Arg Ser Cys Gln Asp Phe Leu Arg Gln Gln Gly Gly
     50                  55                  60

Gly Arg Arg Glu Ile Leu Glu Asn Gln Trp Gly Arg Glu Gln Gly Leu
 65                  70                  75                  80

Glu Glu Cys Cys Arg Gln Leu Arg Asn Val Glu Glu Gln Cys Arg Cys
                 85                  90                  95

Asp Ala Leu Glu Glu Val Ala Arg Glu Val Gln Ser Gln Gln His Gly
             100                 105                 110

Gln Gln Gly Ser Gln Ile Leu Gln His Ala Arg Met Leu Pro Ser Met
            115                 120                 125

Cys Gln Ile Arg Pro Gln Arg Cys Asp Phe
130                 135
```